US009309239B2

(12) United States Patent
Follmann et al.

(10) Patent No.: US 9,309,239 B2
(45) Date of Patent: Apr. 12, 2016

(54) SUBSTITUTED 6-FLUORO-1H-PYRAZOLO[4,3-B]PYRIDINES AND USE THEREOF

(75) Inventors: Markus Follmann, Köln (DE); Johannes-Peter Stasch, Solingen (DE); Gorden Redlich, Bochum (DE); Jens Ackerstaff, Berlin (DE); Nils Griebenow, Dormagen (DE); Andreas Knorr, Erkrath (DE); Frank Wunder, Wuppertal (DE); Volkhart Min-Jian Li, Velbert (DE); Joachim Mittendorf, Wuppertal (DE); Karl-Heinz Schlemmer, Wuppertal (DE); Rolf Jautelat, Haan (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 101 days.

(21) Appl. No.: 13/882,118

(22) PCT Filed: Nov. 3, 2011

(86) PCT No.: PCT/EP2011/069346
§ 371 (c)(1),
(2), (4) Date: Jun. 18, 2013

(87) PCT Pub. No.: WO2012/059549
PCT Pub. Date: May 10, 2012

(65) Prior Publication Data
US 2013/0267548 A1  Oct. 10, 2013

(30) Foreign Application Priority Data
Nov. 4, 2010  (DE) .......................... 10 2010 043 379

(51) Int. Cl.
*C07D 471/04*  (2006.01)
*A61K 31/506*  (2006.01)
*A61K 45/06*  (2006.01)

(52) U.S. Cl.
CPC ............ *C07D 471/04* (2013.01); *A61K 31/506* (2013.01); *A61K 45/06* (2013.01)

(58) Field of Classification Search
CPC ..... C07D 471/04; A61K 31/506; A61K 45/06
See application file for complete search history.

(56) References Cited

U.S. PATENT DOCUMENTS

| 6,180,656 B1 | 1/2001 | Furstner et al. |
| 6,451,805 B1 | 9/2002 | Straub et al. |
| 6,693,102 B2 | 2/2004 | Stasch et al. |
| 6,743,798 B1 | 6/2004 | Straub et al. |
| 6,833,364 B1 | 12/2004 | Straub et al. |
| 6,903,089 B1 | 6/2005 | Stasch et al. |
| 6,919,345 B2 | 7/2005 | Stasch et al. |
| 7,105,523 B2 | 9/2006 | Stasch et al. |
| 7,173,037 B2 | 2/2007 | Alonso-Alija et al. |
| 7,226,941 B2 | 6/2007 | Park et al. |
| 7,410,973 B2 | 8/2008 | Feurer et al. |
| 8,242,272 B2 | 8/2012 | Jimenez et al. |
| 8,309,551 B2 | 11/2012 | Schirok et al. |
| 8,334,291 B2 | 12/2012 | Schirok et al. |
| 8,492,544 B2 | 7/2013 | Mais et al. |
| 8,501,945 B2 | 8/2013 | Mais et al. |
| 8,802,847 B2 | 8/2014 | Fey |
| 8,921,377 B2 | 12/2014 | Follmann et al. |
| 2004/0235863 A1 | 11/2004 | Feurer et al. |
| 2006/0167016 A1 | 7/2006 | Feurer et al. |
| 2007/0225299 A1 | 9/2007 | Bischoff et al. |
| 2010/0029653 A1* | 2/2010 | Schirok et al. ................ 514/245 |
| 2011/0183999 A1 | 7/2011 | Grunenberg et al. |
| 2011/0224197 A1 | 9/2011 | Henkel et al. |
| 2012/0022084 A1 | 1/2012 | Follmann et al. |
| 2012/0029002 A1 | 2/2012 | Straub et al. |
| 2013/0143900 A1 | 6/2013 | Fey |
| 2013/0211090 A1 | 8/2013 | Follmann et al. |
| 2013/0267548 A1 | 10/2013 | Follmann et al. |
| 2014/0315926 A1 | 10/2014 | Fey et al. |

FOREIGN PATENT DOCUMENTS

| CA | 2 809 911 A1 | 3/2012 |
| WO | WO 2008031513 A1 * | 3/2008 |
| WO | 2009/000832 A2 | 12/2008 |

OTHER PUBLICATIONS

Becker et al., "NO-independent regulatory site of direct sGC stimulators like YC-1 and BAY 41-2272," BMC Pharmacology, (Dec. 28, 2001), vol. 1, No. 13, pp. 1-12.
Cheng et al., "Potential Purine Antagonists VII. Synthesis of 6-Alkylpyrazolo-[3,4-d]pyrimidines," The Journal of Organic Chemistry, (Feb. 1958), vol. 23, No. 2, pp. 191-200.
Evgenov et al., "NO-independent Stimulators and Activators of Soluble Guanylate Cyclase: Discovery and Therapeutic Potential," Nature Reviews Drug Discovery, (Sep. 2006), vol. 5, No. 9, pp. 755-768.
Follmann et al., U.S. Appl. No. 13/882,123, entitled "Benzyl-substituted carbamates and use thereof," filed May 29, 2013.
Glass et al., "Stimulation of Human Platelet Guanylate Cyclase by Fatty Acids," The Journal of Biological Chemistry, (Feb. 25, 1977), vol. 252, No. 4, pp. 1279-1285.
Greene et al., "The cGMP Signaling Pathway as a Therapeutic Target in Heart Failure with Preserved Ejection Fraction," Journal of the American Heart Association, (Dec. 11, 2013), vol. 2, No. 6, pp. 1-11.
Ko et al., "YC-1, a Novel Activator of Platelet Guanylate Cyclase," Blood, (Dec. 15, 1994), vol. 84, No. 12, pp. 4226-4233.

(Continued)

*Primary Examiner* — Sarah Pihonak
(74) *Attorney, Agent, or Firm* — Buchanan Ingersoll & Rooney

(57) ABSTRACT

The present application relates to novel substituted 6-fluoro-1H-pyrazolo[4,3-b]pyridines, to processes for preparation thereof, to the use thereof, alone or in combinations, for treatment and/or prophylaxis of diseases and to the use thereof for preparing Medicaments for the treatment and/or prophylaxis of diseases, especially for treatment and/or prophylaxis of cardiovascular disorders.

8 Claims, No Drawings

(56) References Cited

OTHER PUBLICATIONS

Mittendorf et al., "Discovery of Riociguat (BAY 63-2521): A Potent, Oral Stimulator of Soluble Guanylate Cyclase for the Treatment of Pulmonary Hypertension," ChemMedChem, (May 2009), vol. 4, No. 5, pp. 853-865.

Mulsch et al., "Effect of YC-1, an NO-independent, Superoxide-Sensitive Stimulator of Soluble Guanylyl Cyclase, on Smooth Muscle Responsiveness to Nitrovasodilators," British Journal of Pharmacology, (Feb. 1997), vol. 120, No. 4, pp. 681-689.

Pettibone et al., "A Structurally Novel Stimulator of Guanylate Cyclase with Long-Lasting Hypotensive Activity in the Dog," European Journal of Pharmacology, (Oct. 22, 1985), vol. 116, No. 3, pp. 307-312.

Sharkovska et al., "Nitric oxide-independent stimulation of soluble guanylate cyclase reduces organ damage in experimental low-renin and high-renin models," Journal of Hypertension, (Aug. 2010), vol. 28, No. 8, pp. 1666-1675.

Stasch et al., "Soluble Guanylate Cyclase as an Emerging Therapeutic Target in Cardiopulmonary Disease," Circulation, (May 24, 2011), vol. 123, No. 20, pp. 2263-2273.

Wunder et al., "A cell-based cGMP assay useful for ultra-high-throughput screening and identification of modulators of the nitric oxide/cGMP pathway," Analytical Biochemistry, (Apr. 1, 2005), vol. 339, No. 1, pp. 104-112.

Wu et al., "YC-1 Inhibited Human Platelet Aggregation Through NO-Independent Activation of Soluble Guanylate Cyclase," British Journal of Pharmacology, (Oct. 1995), vol. 116, No. 3, pp. 1973-1978.

Yu et al., "Vasorelaxant Effect of Isoliquiritigenin, a Novel Soluble Guanylate Cyclase Activator, in Rat Aorta," British Journal of Pharmacology, (Apr. 1995), vol. 114, No. 38, pp. 1587-1594.

International Search Report issued on Dec. 23, 2011, by the European Patent Office as the International Searching Authority in corresponding International Application No. PCT/EP2011/069346. (5 pages).

Notification Concerning Transmittal of International Preliminary Report on Patentability (Forms PCT/IB/326 and PCT/IB/373) and the Written Opinion of the International Searching Authority (Form PCT/ISA/237) issued on May 7, 2013, in corresponding International Application No. PCT/EP2011/069346. (13 pages).

Ghofrani et al., "Soluble Guanylate Cyclase Stimulation: an Emerging Option in Pulmonary Hypertension Therapy," European Respiratory Review, (Mar. 1, 2009), vol. 18, No. 111, pp, 35-41.

* cited by examiner

SUBSTITUTED 6-FLUORO-1H-PYRAZOLO[4,3-B]PYRIDINES AND USE THEREOF

The present application relates to novel substituted 6-fluoro-1H-pyrazolo[4,3-b]pyridines, to processes for preparation thereof, to the use thereof, alone or in combinations, for treatment and/or prophylaxis of diseases and to the use thereof for preparing medicaments for the treatment and/or prophylaxis of diseases, especially for treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be divided into two groups either according to structural features or according to the type of ligands: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. It is of central importance for the activation mechanism. NO is able to bind to the iron atom of heme and thus markedly increase the activity of the enzyme. Heme-free preparations cannot, by contrast, be stimulated by NO. Carbon monoxide (CO) is also able to attach to the central iron atom of heme, but the stimulation by CO is distinctly less than that by NO.

By forming cGMP, and owing to the resulting regulation of phosphodiesterases, ion channels and protein kinases, guanylate cyclase plays a crucial role in different physiological processes, more particularly in the relaxation and proliferation of smooth muscle cells, in platelet aggregation and platelet adhesion, and in neuronal signal transmission, and also in the event of disorders based on disruption of the abovementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, myocardial infarction, thromboses, stroke and sexual dysfunction.

Owing to the expected high efficiency and few side effects, a treatment of such disorders which targets the influence of the cGMP signal path in organisms and is NO-independent is a promising approach.

Therapeutic stimulation of soluble guanylate cyclase has to date been accomplished using exclusively compounds such as organic nitrates, the effect of which is based on NO. The latter is formed by bioconversion and activates soluble guanylate cyclase by attack at the central iron atom of heme. In addition to the side effects, the development of tolerance is one of the crucial disadvantages of this mode of treatment.

In recent years, some substances have been described which stimulate soluble guanylate cyclase directly, i.e. without prior release of NO, such as, for example 3-(5'-hydroxymethyl-2'-furyl)-1-benzylindazole [YC-1; Wu et al., *Blood* 84 (1994), 4226; Mülsch et al., *Brit. J. Pharmacol.* 120 (1997), 681], fatty acids [Goldberg et al., *J. Biol. Chem.* 252 (1977), 1279], diphenyliodonium hexafluorophosphate [Pettibone et al., *Eur. J. Pharmacol.* 116 (1985), 307], isoliquiritigenin [Yu et al., *Brit. J. Pharmacol.* 114 (1995), 1587] and various substituted pyrazole derivatives (WO 98/16223).

WO 2008/031513 discloses inter alia 1H-pyrazolo[4,3-b] pyridines as stimulators of soluble guanylate cyclase for the treatment of cardiovascular disorders. WO 2005/030121 describes fused pyrazoles for the treatment of cancer diseases. WO 2011/119518 and WO 2011/115804 disclose carbamate-substituted pyrimidines for the treatment of cardiovascular disorders.

It is an object of the present invention to provide novel substances which act as stimulators of soluble guanylate cyclase and which have an identical or improved therapeutic profile compared to compounds known from the prior art, for example with respect to their in vivo properties such as their pharmacokinetic and pharmacodynamic behavior and/or their dose-activity relationship.

The present invention provides compounds of the general formula (I)

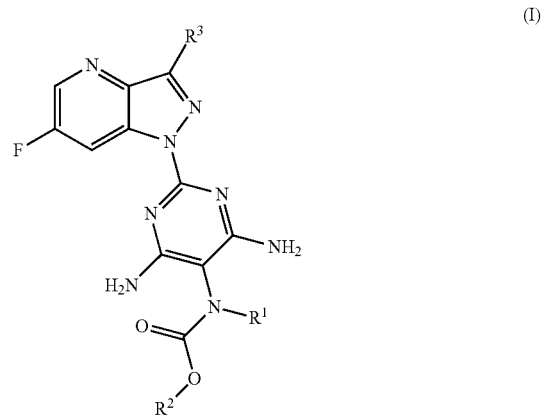

in which
$R^1$ represents hydrogen or $(C_1-C_4)$-alkyl,
   where $(C_1-C_4)$-alkyl may be substituted by one or two substituents independently of one another selected from the group consisting of fluorine and trifluoromethyl,
$R^2$ represents $(C_1-C_4)$-alkyl, $(C_3-C_7)$-cycloalkyl or a 4- to 7-membered heterocycle,
   where $(C_1-C_4)$-alkyl may be substituted by one or two substituents independently selected from the group consisting of fluorine, trifluoromethyl and $(C_3-C_7)$-cycloalkyl,
$R^3$ represents $(C_1-C_6)$-alkyl or benzyl,
   where $(C_1-C_6)$-alkyl is substituted by one trifluoromethyl substituent,
   where $(C_1-C_6)$-alkyl may be substituted by 1 to 3 fluorine substituents, and
   where benzyl is substituted by 1 to 3 fluorine substituents,
and the N-oxides, salts, solvates, salts of N-oxides and solvates of the N-oxides or salts thereof.

Compounds according to the invention are the compounds of the formula (I) and their salts, solvates and solvates of the salts, the compounds, comprised by formula (I), of the formulae mentioned below and their salts, solvates and solvates of the salts and the compounds comprised by formula (I), mentioned below as embodiments, and their salts, solvates and solvates of the salts, if the compounds, comprised by formula (I), mentioned below are not already salts, solvates and solvates of the salts.

In the context of the present invention, preferred salts are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in the solid or liquid state, form a complex by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than that which occurs usually or predominantly in nature. Examples of isotopes which can be incorporated into a compound according to the invention are those of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}F$, $^{33}F$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, such as, more particularly, those in which one or more radioactive isotopes have been incorporated, may be of benefit, for example, for the study of the mechanism of action or of the active compound distribution in the body; due to the comparative ease of preparability and detectability, compounds labeled particularly with $^{3}H$ or $^{14}C$ isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the compounds according to the invention may therefore, in some cases, also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Moreover, the present invention also encompasses prodrugs of the compounds according to the invention. Here, the term "prodrugs" refers to compounds which for their part can be biologically active or inactive, but are converted (for example metabolically or hydrolytically) into compounds according to the invention during their dwell time in the body.

In the context of the present invention, the substituents, unless specified otherwise, are each defined as follows:

Alkyl in the context of the invention is a linear or branched alkyl radical having 1 to 4 carbon atoms. The following may be mentioned by way of example and by way of preference: methyl, ethyl, n-propyl, isopropyl, n-butyl, isobutyl, 1-methylpropyl, tert-butyl.

Cycloalkyl in the context of the invention is a monocyclic saturated carbocycle having 3 to 7 ring carbon atoms. The following may be mentioned by way of example and by way of preference: cyclopropyl, cyclobutyl, cyclopentyl, cyclohexyl and cycloheptyl.

Heterocycle in the context of the invention is a saturated heterocycle having a total of 4 to 7 ring atoms, which contains one or two ring heteroatoms from the group of N, O and/or S and is joined via a ring carbon atom. The following may be mentioned by way of example: azetidinyl, pyrrolidinyl, pyrazolidinyl, tetrahydrofuranyl, piperidinyl, piperazinyl, tetrahydropyranyl, morpholinyl, thiomorpholinyl and azepanyl. Preference is given to azetidinyl, pyrrolidinyl, tetrahydrofuranyl, piperidinyl, piperazinyl, tetrahydropyranyl and morpholinyl. Particular preference is given to azetidinyl, pyrrolidinyl, piperidinyl and morpholinyl.

Halogen in the context of the invention is fluorine, chlorine, bromine and iodine.

If radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, preference is given to compounds of the formula (I) in which $R^1$ represents hydrogen, methyl or ethyl,
    where methyl may be substituted by a trifluoromethyl substituent,
$R^2$ represents methyl, ethyl, isopropyl, cyclopropyl, cyclobutyl or oxetanyl,
    where methyl and ethyl may be substituted by one or two substituents independently of one another selected from the group consisting of fluorine, trifluoromethyl and cyclopropyl,
$R^3$ represents 3,3,3-trifluoroprop-1-yl, 3,3,4,4,4-pentafluorobut-1-yl or benzyl,
    where benzyl is substituted by 1 or 2 fluorine substituents,
and the salts, solvates and solvates of the salts thereof.

In the context of the present invention, particular preference is given to compounds of the formula (I) in which $R^1$ represents hydrogen, methyl, ethyl or 2,2,2-trifluoroethyl,
$R^2$ represents methyl, ethyl or cyclopropylmethyl,
$R^3$ represents 2-fluorobenzyl,
and the salts, solvates and solvates of the salts thereof.

In the context of the present invention, preference is also given to compounds of the formula (I) in which
R¹ represents hydrogen, methyl or ethyl,
where methyl may be substituted by a trifluoromethyl substituent,
R² represents methyl, ethyl, isopropyl, cyclopropyl, cyclobutyl or oxetanyl,
where methyl and ethyl may be substituted by one or two substituents independently of one another selected from the group consisting of fluorine, trifluoromethyl and cyclopropyl,
R³ represents 2-fluorobenzyl,
and the salts, solvates and solvates of the salts thereof.

In the context of the present invention, preference is also given to compounds of the formula (I) in which
R¹ represents hydrogen, methyl, ethyl or 2,2,2-trifluoroethyl,
and the salts, solvates and solvates of the salts thereof.

In the context of the present invention, preference is also given to compounds of the formula (I) in which
R² represents methyl, ethyl or cyclopropylmethyl,
and the salts, solvates and solvates of the salts thereof.

In the context of the present invention, preference is also given to compounds of the formula (I) in which
R³ represents 2-fluorobenzyl,
and the salts, solvates and solvates of the salts thereof.

In the context of the present invention, preference is also given to compounds of the formula (I) in which
R³ represents 3,3,3-trifluoroprop-1-yl or 3,3,4,4,4-pentafluorobut-1-yl,
and the salts, solvates and solvates of the salts thereof.

The individual radical definitions specified in the particular combinations or preferred combinations of radicals are, independently of the particular combinations of the radicals specified, also replaced as desired by radical definitions of other combinations.

Particular preference is given to combinations of two or more of the preferred ranges mentioned above.

The invention further provides a process for preparing the compounds of the formula (I) according to the invention, characterized in that a compound of the formula (II)

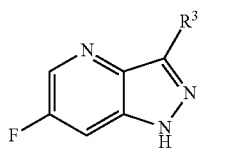

(II)

in which R³ has the meaning given above
[A] is reacted in an inert solvent in the presence of a suitable base with the compound of the formula (III)

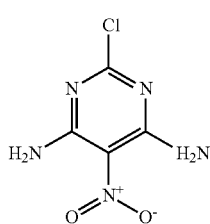

(III)

to give a compound of the formula (IV)

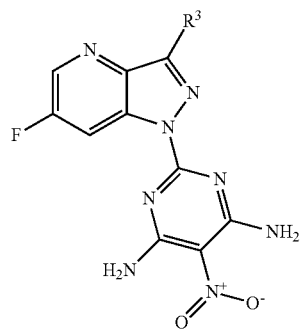

(IV)

in which R³ has the meaning given above,
this is then reduced in an inert solvent with a suitable reducing agent to give a compound of the formula (V)

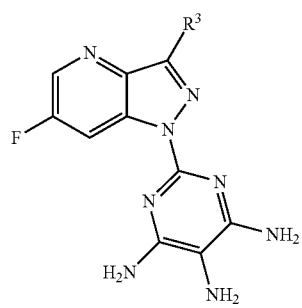

(V)

in which R³ has the meaning given above,
and this is then reacted in the presence of a suitable base in the presence or absence of a solvent with a compound of the formula (VI)

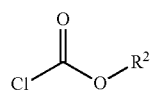

(VI)

in which R² has the meaning given above,
to give a compound of the formula (I-A)

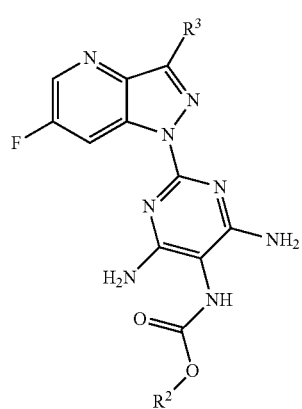

(I-A)

in which R² and R³ each have the meanings given above, or

[B] a compound of the formula (II) is converted in an inert solvent under acidic conditions with amino acetonitrile into a compound of the formula (VII)

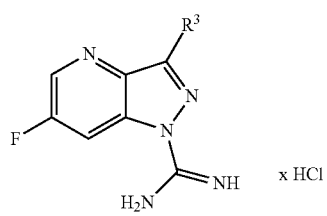
(VII)

in which R³ has the meaning given above, this is subsequently reacted in an inert solvent in the presence of a suitable base with the compound of the formula (VIII)

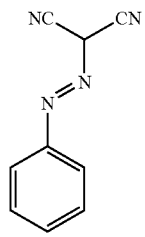
(VIII)

to give a compound of the formula (IX)

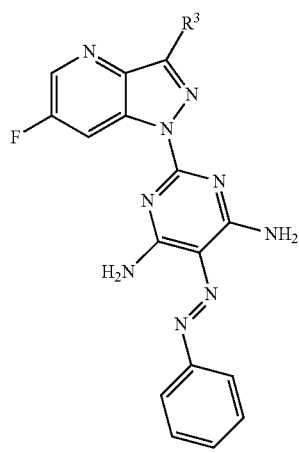
(IX)

in which R³ has the meaning given above and this is then reduced in an inert solvent in the presence of a suitable reducing agent to give the compound (V), and this is subsequently reacted further according to process [A] to give a compound (I-A), or

[C] a compound of the formula (I-A) is reacted in an inert solvent with a compound of the formula (X)

R¹—X¹    (X)

in which R¹ has the meaning given above and

X¹ is a suitable leaving group, for example halogen, tosylate or mesylate, especially bromine or iodine, to give a compound of the formula (I-B)

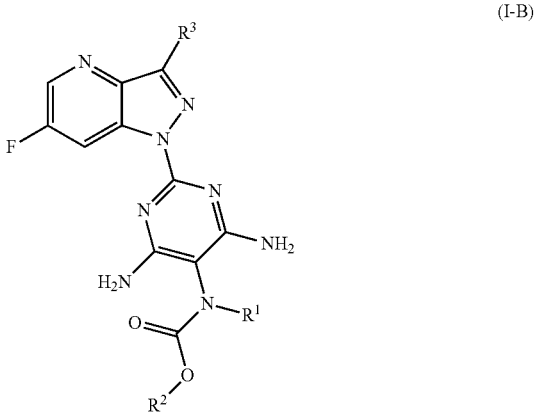
(I-B)

in which R¹, R² and R³ are each as defined above, and the resulting compounds of the formulae (I-A) and (I-B) are, where appropriate, converted with the appropriate (i) solvents and/or (ii) acids or bases into their solvates, salts and/or solvates of the salts.

The compounds of the formulae (I-A) and (I-B) together form the group of the compounds of the formula (I) according to the invention.

Inert solvents for the process step (II)+(III)→(IV) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), dimethylacetamide, N-methylpyrrolidone (NMP), pyridine, acetonitrile, sulfolane or else water. It is also possible to use mixtures of the solvents mentioned. Preference is given to dioxane.

Suitable bases for the process step (II)+(III)→(I) are alkali metal hydrides such as sodium hydride, alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, amides such as sodium amide, lithium bis(trimethylsilyl)amide, sodium bis(trimethylsilyl)amide or potassium bis(trimethylsilyl)amide or lithium diisopropylamide, organometallic compounds such as butyllithium or phenyllithium, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to lithium bis(trimethylsilyl)amide or sodium hydride.

The reaction (II)+(III)→(IV) is generally carried out in a temperature range of from +20° C. to +180° C., preferably at from +50° C. to +120° C., if appropriate in a microwave. The reaction can be carried out at atmospheric, elevated or reduced pressure (for example from 0.5 to 5 bar). In general, atmospheric pressure is employed.

The reductions (IV)→(V) and (IX)→(V) are carried out in the presence of a suitable catalyst in an inert solvent in a temperature range of from +20° C. to +40° C. under hydrogen atmospheric pressure.

Inert solvents for the reductions (IV)→(V) and (IX)→(V) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is also possible to use mixtures of the solvents mentioned. Preference is given to DMF and pyridine.

Suitable catalysts for the reactions (IV)→(V) and (IX)→(V) are, for example, palladium on activated carbon, platinum on carbon, palladium hydroxide or Raney nickel.

Alternatively, the reductions (IV)→(V) and (IX)→(V) can be carried out using a metal or metal salt such as, for example, iron, zinc or tin(II) chloride in a suitable acid such as, for example, hydrogen chloride/hydrochloric acid, sulfuric acid, phosphoric acid or acetic acid in a temperature range of from +20° C. to +140° C.

Inert solvents for the process step (V)+(VI)→(I-A) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, halogenated hydrocarbons such as dichloromethane, trichloromethane, carbon tetrachloride, trichloroethylene or chlorobenzene, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), acetonitrile or else water. It is also possible to use mixtures of the solvents mentioned. Preference is given to dimethylformamide and toluene and also to a mixture of dimethylformamide and toluene.

Suitable bases for the process step (V)+(VI)→(I-A) are alkali metal hydrides such as sodium hydride, alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, amides such as sodium amide, lithium bis(trimethylsilyl)amide, sodium bis(trimethylsilyl)amide or potassium bis(trimethylsilyl)amide or lithium diisopropylamide, organometallic compounds such as butyllithium or phenyllithium, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to pyridine.

The reaction (V)+(VI)→(I-A) is generally carried out in a temperature range from −10° C. to +30° C., preferably at from 0° C. to +20° C. The reaction can be carried out at atmospheric, elevated or reduced pressure (for example from 0.5 to 5 bar). The reaction is generally carried out at atmospheric pressure.

Inert solvents for the process step (VII)+(VIII)→(IX) are alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is also possible to use mixtures of the solvents mentioned. Preference is given to DMF.

Inert solvents for the process step (II)→(VII) are alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine or else water. It is also possible to use mixtures of the solvents mentioned. Preference is given to DMF.

Suitable acids are, for example, inorganic acids such as sulfuric acid, hydrogen chloride/hydrochloric acid, polyphosphoric acid or phosphoric acid, organic acids such as acetic acid, trifluoroacetic acid, methanesulfonic acid, toluenesulfonic acid. Preference is given to hydrogen chloride/hydrochloric acid.

The reaction (II)→(VII) is generally carried out in a temperature range from −10° C. to +30° C., preferably at from 0° C. to +20° C. The reaction can be carried out at atmospheric, elevated or reduced pressure (for example from 0.5 to 5 bar). The reaction is generally carried out at atmospheric pressure.

Suitable bases for the process step (VII)+(VIII)→(IX) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine.

The reaction (VII)+(VIII)→(IX) is generally carried out in a temperature range of from +20° C. to +150° C., preferably at from +80° C. to +120° C., if appropriate in a microwave. The reaction can be effected at standard, elevated or reduced pressure (for example from 0.5 to 5 bar). The reaction is generally carried out at atmospheric pressure.

The compound of the formula (VIII) can be prepared analogously to the literature L. F. Cavalieri, J. F. Tanker, A. Bendich, J. Am. Chem. Soc., 1949, 71, 533.

Inert solvents for the process step (I-A)+(X)→(I-B) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, halogenated hydrocarbons such as dichloromethane, trichloromethane, carbon tetrachloride, trichloroethylene or chlorobenzene, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), acetonitrile or else water. It is also possible to use mixtures of the solvents mentioned. Preference is given to THF.

Suitable bases for the process step (I-A)+(X)→(I-B) are alkali metal hydrides such as sodium hydride, alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, amides such as sodium amide, lithium bis(trimethylsilyl)amide, sodium bis(trimethylsilyl)amide or potassium bis(trimethylsilyl)amide or lithium diisopropylamide, organometallic compounds such as butyllithium or phenyllithium, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to lithium bis(trimethylsilyl)amide or sodium hydride.

The reaction (I-A)+(X)→(I-B) is generally carried out in a temperature range from −10° C. to +30° C., preferably at from 0° C. to +20° C. The reaction can be carried out at atmospheric, elevated or reduced pressure (for example from 0.5 to 5 bar). The reaction is generally carried out at atmospheric pressure.

The preparation processes described are illustrated by way of example by the synthesis schemes below (Schemes 1 to 3):

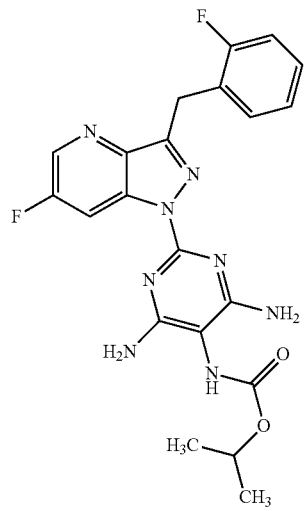

[a): NaH, DMF; b) H₂, Pd—C; c) pyridine].

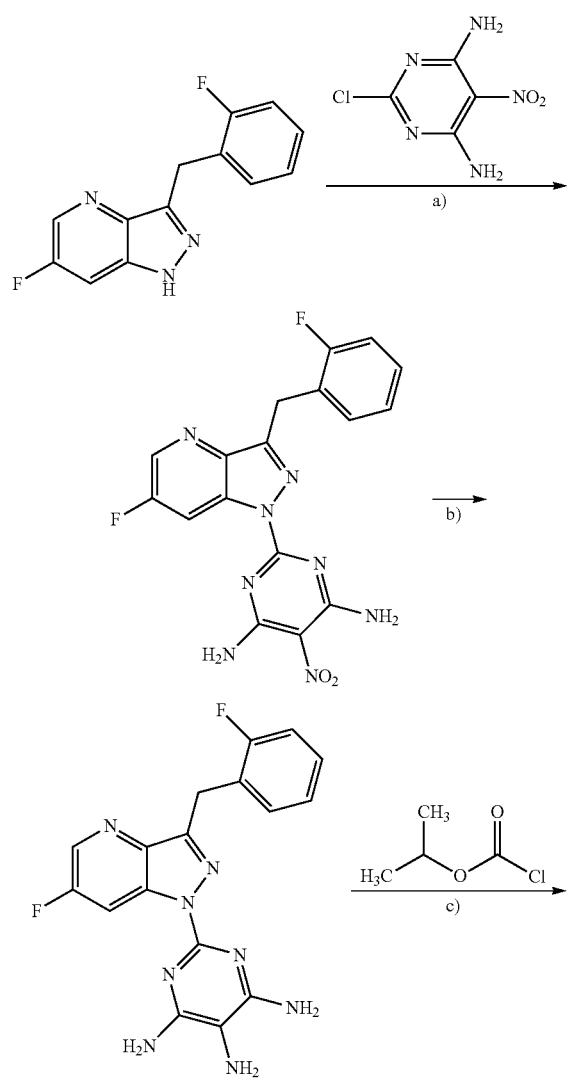

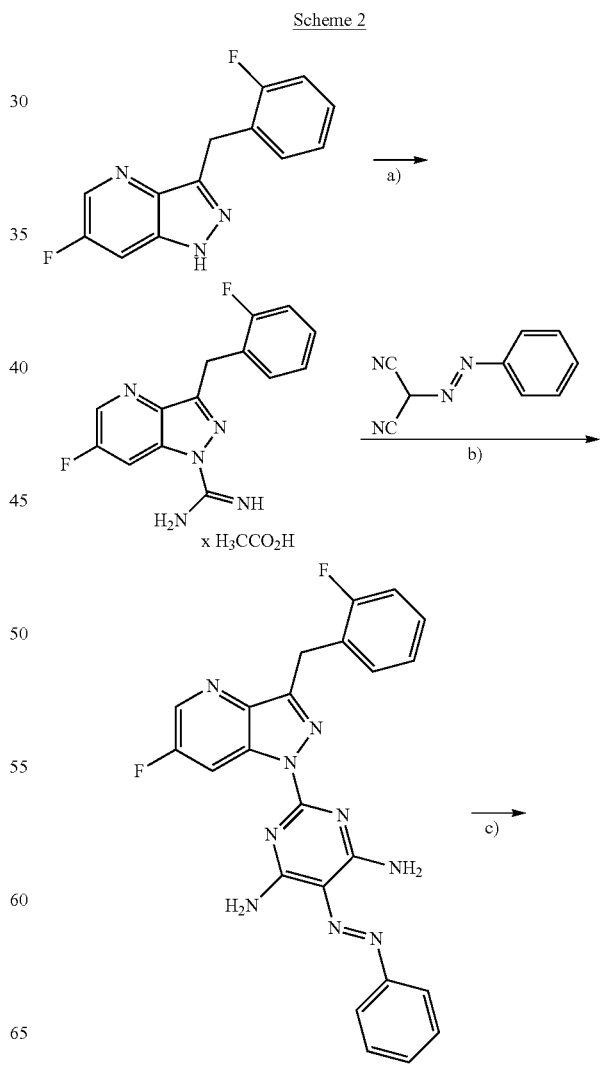

-continued

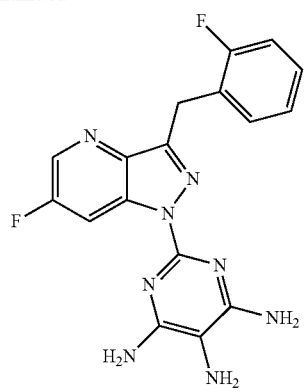

[a]: aminoacetonitrile, HCl, dioxane; b): triethylamine; c): H₂, Pd—C].

Scheme 3

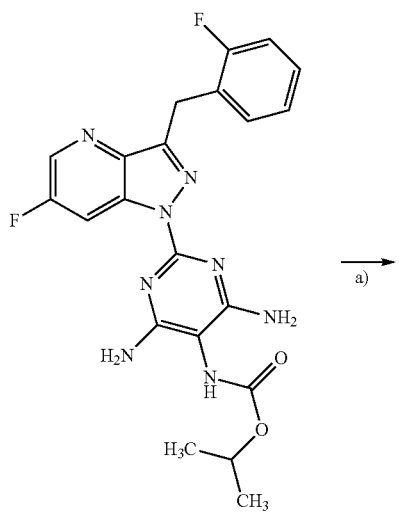

[a) LiHMDS, methyl iodide, THF].

The compound of the formula (II) can be prepared by initially converting the compound of the formula (XI)

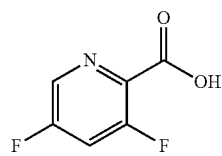
(XI)

with thionyl chloride into the corresponding acid chloride, then reacting the latter in an inert solvent in the presence of a suitable base with a compound of the formula (XII)

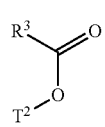
(XII)

in which $R^3$ has the meaning given above and
$T^2$ represents $(C_1\text{-}C_4)$-alkyl
to give a compound of the formula (XIII)

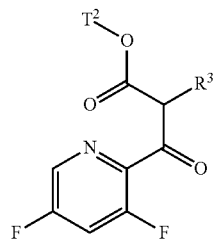
(XIII)

in which $R^3$ and $T^2$ each have the meanings given above, then decarboxylating this in an inert solvent to give a compound of the formula (XIV)

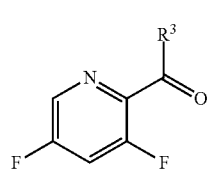
(XIV)

in which $R^3$ has the meaning given above
and then cyclizing the latter in an inert solvent with hydrazine hydrate.

Inert solvents for the process step (XI)+(XII)→(XIII) are, for example, ethers such as diethyl ether, dioxane, tetrahydrofuran, glycol dimethyl ether or diethylene glycol dimethyl ether, halogenated hydrocarbons such as dichloromethane, trichloromethane, carbon tetrachloride, trichloroethylene or chlorobenzene, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP) or acetonitrile. It is also possible to use mixtures of the solvents mentioned. Preference is given to THF.

Suitable bases for the process step (XI)+(XII)→(XIII) are alkali metal hydrides such as sodium hydride, alkali metal alkoxides such as sodium methoxide or potassium methoxide, sodium ethoxide or potassium ethoxide or potassium tert-butoxide, amides such as sodium amide, lithium bis(trimethylsilyl)amide, sodium bis(trimethylsilyl)amide or potassium bis(trimethylsilyl)amide or lithium diisopropylamide, organometallic compounds such as butyllithium or phenyllithium. Preference is given to lithium bis(trimethylsilyl)amide.

The reaction (XI)+(XII)→(XIII) is generally carried out in a temperature range from −78° C. to +30° C., preferably at from −78° C. to +20° C. The reaction can be carried out at atmospheric, elevated or reduced pressure (for example from 0.5 to 5 bar). The reaction is generally carried out at atmospheric pressure.

The decarboxylation (XIII)→(XIV) is carried out in an inert solvent using lithium chloride or sodium chloride.

Inert solvents for the decarboxylation (XIII)→(XIV) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is also possible to use mixtures of the solvents mentioned. Preference is given to a mixture of DMSO and water.

The reaction (XIII)→(XIV) is generally carried out in a temperature range from +100° C. to +200° C., preferably at +120° C. to +160° C., if appropriate in a microwave. The reaction can be carried out at atmospheric, elevated or reduced pressure (for example from 0.5 to 5 bar).

Inert solvents for the process step (XIV)→(II) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine or acetonitrile. It is also possible to use mixtures of the solvents mentioned. Preference is given to pyridine, if appropriate with addition of catalytic amounts of N,N-dimethylaminopyridine.

The reaction (XIV)→(II) is generally carried out in a temperature range from +60° C. to +200° C., preferably at from +120° C. to +180° C. The reaction can be carried out at atmospheric, elevated or reduced pressure (for example from 0.5 to 5 bar). The reaction is generally carried out at atmospheric pressure.

The process described above is illustrated by way of example by the scheme below (Scheme 4):

Scheme 4

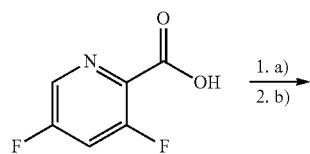

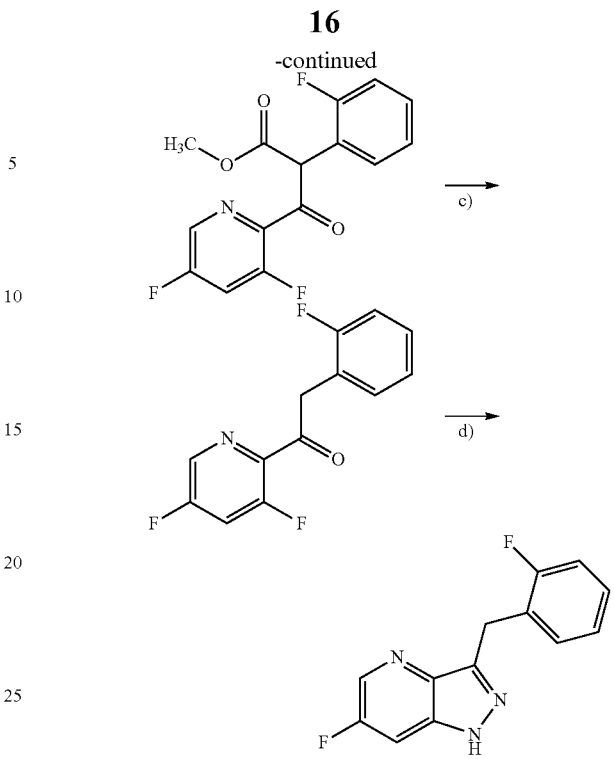

[a]: thionyl chloride; b): LiHMDS, methyl 2-fluorophenylacetate; c): NaCl, water; d): hydrazine, pyridine].

The compounds according to the invention act as stimulators of soluble guanylate cyclase, have useful pharmacological properties and have an improved pharmacokinetic and/or pharmacodynamic profile. They are therefore suitable for the treatment and/or prophylaxis of diseases in man and animals.

The compounds according to the invention cause vasorelaxation and inhibition of platelet aggregation, and lead to a decrease in blood pressure and to a rise in coronary blood flow. These effects are mediated by direct stimulation of soluble guanylate cyclase and an intracellular rise in cGMP. In addition, the compounds according to the invention enhance the action of substances which increase the cGMP level, for example EDRF (endothelium-derived relaxing factor), NO donors, protoporphyrin IX, arachidonic acid or phenylhydrazine derivatives.

Accordingly, the compounds according to the invention can be used in medicaments for the treatment and/or prophylaxis of cardiovascular disorders such as, for example, hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, Sick-Sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), cardiogenic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, shock cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term heart failure also includes more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

In addition, the compounds according to the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinaemias, sitosterolaemia, xanthomatosis, Tangier disease, adipositas, obesity and of combined hyperlipidaemias and metabolic syndrome.

The compounds according to the invention can additionally be used for the treatment and/or prophylaxis of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and femal urogenital system.

The compounds according to the invention are furthermore suitable for the treatment and/or prophylaxis of kidney disorders, in particular of acute and chronic renal insufficiency and acute and chronic renal failure In the context of the present invention, the term renal insufficiency comprises both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminurea, macroalbuminurea, laesions on glomerulae and arterioles, tubular dilatation, hyperphosphataemia and/or need for dialysis. The present invention also comprises the use of the compounds according to the invention for the treatment and/or prophylaxis of sequelae of renal insufficiency, for example pulmonary edema, heart failure, uremia, anemia, electrolyte disturbances (for example hyperkalemia, hyponatremia) and disturbances in bone and carbohydrate metabolism.

Furthermore, the compounds according to the invention are also suitable for the treatment and/or prophylaxis of asthmatic disorders, pulmonary arterial hypertension (PAH) and other forms of pulmonary hypertension (PH), chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention also represent active compounds for controlling central nervous system diseases characterized by disturbances of the NO/cGMP system. More particularly, they are suitable for improving perception, concentration, learning or memory after cognitive impairments such as those occurring particularly in the event of situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children having learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis. They are also suitable for treatment and/or prophylaxis of central nervous system disorders such as states of anxiety, tension and depression, CNS-related sexual dysfunction and disrupted sleep, and for control of pathological disturbances of the intake of food, stimulants and addictive substances.

Furthermore, the compounds according to the invention are also suitable for regulating cerebral blood flow and are thus effective agents for the control of migraine. They are also suitable for prophylaxis and control of sequelae of cerebral infarct (*Apoplexia cerebri*) such as stroke, cerebral ischemia and skull-brain trauma. The compounds according to the invention can likewise be employed for controlling states of pain and tinnitus.

In addition, the compounds according to the invention have antiinflammatory action and can therefore be used as antiinflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the compounds according to the invention can also be used for the treatment and/or prophylaxis of autoimmune diseases.

The compounds according to the invention are furthermore suitable for the treatment and/or prophylaxis of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy and proliferative vitroretinopathy.

The compounds according to the invention are furthermore suitable for controlling postoperative scarring, for example as a result of glaucoma operations.

The compounds according to the invention can also be used cosmetically for ageing and keratinized skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, in particular the disorders mentioned above.

The present invention further provides the compounds according to the invention for use in a method for the treatment and/or prophylaxis of heart failure, angina pectoris, hypertension, pulmonary hypertension, ischaemias, vascular disorders, thromboembolic disorders and arteriosclerosis.

The present invention further provides for the use of the compounds according to the invention for producing a medicament for treatment and/or prophylaxis of disorders, in particular the disorders mentioned above.

The present invention further provides a method for treatment and/or prophylaxis of disorders, in particular the disorders mentioned above, using an effective amount of at least one of the compounds according to the invention.

The compounds according to the invention can be employed alone or, if required, in combination with other active compounds. The present invention further provides medicaments comprising at least one of the compounds according to the invention and one or more further active compounds, especially for the treatment and/or prophylaxis of the aforementioned disorders. Preferred examples of suitable active compound combinations include:

organic nitrates and NO donors, for example sodium nitroprusside, nitroglycerine, isosorbide mononitrate, isosorbide dinitrate, molsidomine or SIN1, and inhaled NO;
compounds which inhibit the breakdown of cyclic guanosine monophosphate (cGMP), for example inhibitors of phosphodiesterases (PDE) 1, 2 and/or 5, in particular PDE 5 inhibitors such as sildenafil, vardenafil and tadalafil;

antithrombotic agents, by way of example and with preference from the group of the platelet aggregation inhibitors, the anticoagulants or the profibrinolytic substances;
hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or
active compounds which modify lipid metabolism, by way of example and with preference from the group of the thyroid receptor agonists, cholesterol synthesis inhibitors, by way of example and with preference HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor such as, by way of example and with preference aspirin, clopidogrel, ticlopidin or dipyridamol.

In a preferred embodiment of the invention, the compounds according to the invention are administered in combination with a thrombin inhibitor such as, by way of example and with preference ximelagatran, dabigatran, melagatran, bivalirudin or clexane.

In a preferred embodiment of the invention, the compounds according to the invention are administered in combination with a GPIIb/IIIa antagonist such as, by way of example and with preference tirofiban or abciximab.

In a preferred embodiment of the invention, the compounds according to the invention are administered in combination with a factor Xa inhibitor, by way of example and with preference rivaroxaban (BAY 59-7939), DU176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP600 or SPP800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a diuretic, by way of example and with preference furosemide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein (a) antagonists.

In a preferred embodiment of the invention, the compounds according to the invention are administered in combination with a CETP inhibitor, by way of example and with preference dalcetrapib, BAY 60-5521, anacetrapib oder CETP vaccine (CETi-1).

In a preferred embodiment of the invention, the compounds according to the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin, or pitavastatin.

In a preferred embodiment of the invention, the compounds according to the invention are administered in combination with a squalene synthesis inhibitor, by way of example and with preference BMS188494 or TAK475.

In a preferred embodiment of the invention, the compounds according to the invention are administered in combination with an ACAT inhibitor, by way of example and with preference avasimibe, melinamide, pactimibe, eflucimibe or SMP797.

In a preferred embodiment of the invention, the compounds according to the invention are administered in combination with an MTP inhibitor, by way of example and with preference implitapide, BMS201038, R103757 or JTT130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 685042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, by way of example and with preference orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT(=IBAT) inhibitors, for example AZD7806, S8921, AK105, BAR11741, SC435 or SC635.

In a preferred embodiment of the invention, the compounds according to the invention are administered in combination with a lipoprotein (a) antagonist, by way of example and with preference gemcabene calcium (CI1027) or nicotinic acid.

The present invention further provides medicaments which comprise at least one compound according to the invention, typically together with one or more inert, nontoxic, pharmaceutically suitable auxiliaries, and for the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds according to the invention can be administered in administration forms suitable for these administration routes.

Suitable administration forms for oral administration are those which work according to the prior art, which release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be accomplished in a manner known per se by mixing with inert nontoxic pharmaceutically suitable auxiliaries. These auxiliaries include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavor and/or odor correctors.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dosage is about 0.01 to 100 mg/kg, preferably about 0.01 to 20 mg/kg and most preferably 0.1 to 10 mg/kg of body weight.

It may nevertheless be necessary where appropriate to deviate from the stated amounts, specifically as a function of the body weight, route of administration, individual response to the active compound, nature of the preparation and time or interval over which administration takes place. For instance, in some cases, less than the aforementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration data for the liquid/liquid solutions are in each case based on volume.

A. EXAMPLES

Abbreviations and Acronyms aq. aqueous solution
calc. calculated
DCI direct chemical ionization (in MS)
DMF dimethylformamide
DMSO dimethyl sulfoxide
eq. equivalent(s)
ESI electrospray ionization (in MS)
Et ethyl
h hour(s)
HPLC high-pressure high-performance liquid chromatography
HRMS high-resolution mass spectrometry
conc. concentrated
LC/MS liquid chromatography-coupled mass spectrometry
LiHMDS lithium hexamethyldisilazide
Me methyl
min minute(s)
MS mass spectrometry
NMR nuclear magnetic resonance spectroscopy
$Pd_2 dba_3$ tris(dibenzylideneacetone)dipalladium
Ph phenyl
RT room temperature
$R_t$ retention time (in HPLC)
THF tetrahydrofuran
UV ultraviolet spectrometry
v/v ratio by volume (of a solution)
XPHOS dicyclohexyl(2',4',6'-triisopropylbiphenyl-2-yl)phosphine LC/MS Methods:

Method 1 (LC-MS):

Instrument: Waters Acquity SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 2 (LC-MS):

Instrument: Micromass Quattro Micro MS with HPLC Agilent Series 1100; column: Thermo Hypersil GOLD 3µ, 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Starting Materials and Intermediates:

Example 1A 3,5-Difluoropyridine-2-carbonyl chloride

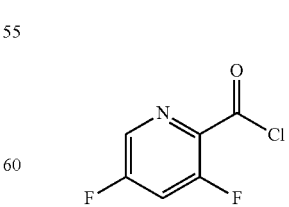

A suspension of 5.00 g (31.4 mmol) of 3,5-difluoropyridine-2-carboxylic acid in thionyl chloride (21 ml) was heated to reflux for 5 h. The solution was concentrated, and the residue was twice taken up in a little toluene and concentrated again. This gave 3.80 g of a solid, which was reacted further directly without further purification.

Example 2A

Methyl 3-(3,5-difluoropyridin-2-yl)-2-(2-fluorophenyl)-3-oxopropanoate

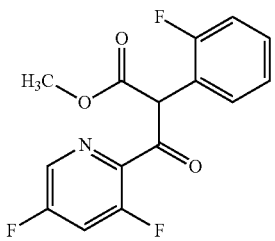 [SMILES: COC(=O)C(C(=O)c1ncc(F)cc1F)c1ccccc1F]

21.4 ml (21.4 mmol) of lithium hexamethyldisilazide (1.0 M in THF) were initially charged in THF (30 ml) under argon and a solution of 3.00 g (17.8 mmol) of methyl 2-fluorophenylacetate in THF (15 ml) was added dropwise at −78° C. The reaction mixture was stirred at −78° C. for 1 h, and then a solution of 3.80 g (21.4 mmol) of the compound from example 1A in THF (15 ml) was added dropwise. The solution was stirred at −78° C. for 1 h, then brought to RT, and saturated aqueous ammonium chloride solution was added in portions. The mixture was diluted with water and extracted twice with ethyl acetate. The combined organic phases were dried over sodium sulfate, filtered and concentrated. The residue was stirred with MTBE, the solid was filtered off and the filtrate was concentrated. Silica gel chromatography (mobile phase:cyclohexane-ethyl acetate: 30:1, 20:1) of the residue gave 3.66 g (87% pure, 57% of theory) of the title compound. The crude product was reacted without further purification.

LC-MS (method 1): $R_t$=1.05 min; MS (ESIpos): m/z=310 (M+H)$^+$.

$^1$H NMR (400 MHz, DMSO-$d_6$): δ=3.66 (s, 3H), 6.25 (s, 1H), 7.20-7.28 (m, 4H), 7.31-7.38 (m, 1H), 8.15-8.23 (m, 1H), 8.68-8.71 (m, 1H).

Example 3A 1-(3,5-Difluoropyridin-2-yl)-2-(2-fluorophenyl)ethanone

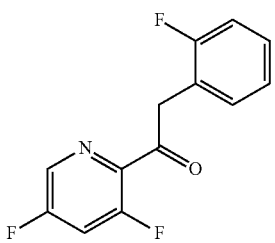 [SMILES: O=C(Cc1ccccc1F)c1ncc(F)cc1F]

11.65 g (37.67 mmol) of the compound from example 2A were initially charged in DMSO (37 ml). Subsequently, 2.42 g (41.44 mmol) of sodium chloride and water (7 ml) were added, and the mixture was stirred in a microwave at 150° C. for 30 min. The reaction mixture was diluted with ethyl acetate, and the organic phase was washed three times with water and once with saturated aqueous sodium chloride solution, dried over sodium sulfate, filtered and concentrated. This gave 9.07 g (89% pure, 85% of theory) of the desired compound as a solid, which was reacted without further purification.

LC-MS (method 1): $R_t$=1.05 min; MS (ESIpos): m/z=252 (M+H)$^+$.

$^1$H NMR (400 MHz, DMSO-$d_6$): δ=4.53 (s, 2H), 7.15-7.22 (m, 2H), 7.30-7.37 (m, 2H), 8.11-8.18 (m, 1H), 8.70-8.72 (m, 1H).

Example 4A

6-Fluoro-3-(2-fluorobenzyl)-1H-pyrazolo[4,3-b]pyridine

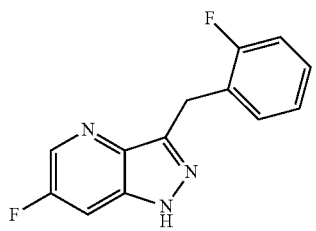 [SMILES: Fc1cnc2c(Cc3ccccc3F)n[nH]c2c1]

9.07 g (32.4 mmol) of the compound from example 3A were initially charged in pyridine (84 ml). Subsequently, 8.10 g (162 mmol) of hydrazine hydrate and 19.8 mg (0.162 mmol) of 4-dimethylaminopyridine were added, and the mixture was heated at reflux for 30 min. The reaction mixture was diluted with ethyl acetate at RT and washed four times with 10% strength aqueous citric acid solution. The organic phase was subsequently washed with saturated aqueous sodium chloride solution, dried over sodium sulfate, filtered and concentrated. MTBE was added to the residue and the solids were filtered off. The latter were dried under high vacuum and gave 1.79 g (79% pure, 18% of theory) of the title compound. The filtrate was concentrated and gave a further 4.86 g (61% pure, 37% of theory) of the title compound. The two fractions were combined and reacted without further purification.

LC-MS (method 2): $R_t$=1.87 min; MS (ESIpos): m/z=246 (M+H)$^+$.

$^1$H NMR (400 MHz, DMSO-d$_6$): δ=4.33 (s, 2H), 7.06-7.12 (m, 1H), 7.12-7.19 (m, 1H), 7.22-7.29 (m, 1H), 7.29-7.35 (m, 1H), 7.87 (dd, 1H), 7.84-7.89 (m, 1H), 8.48-8.51 (br. s, 1H).

Example 5A

2-[6-Fluoro-3-(2-fluorobenzyl)-1H-pyrazolo[4,3-b]pyridin-1-yl]-5-nitropyrimidine-2-diamine

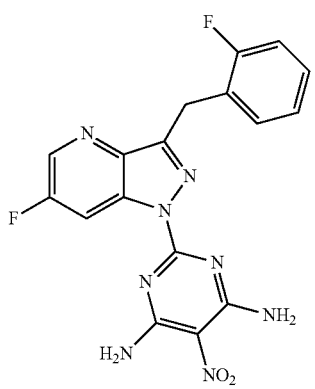

156 mg (about 66% pure, 0.636 mmol) of the compound from example 4A were dissolved in DMF (3.5 ml), 28 mg (0.70 mmol) of sodium hydride (60% in mineral oil) were then added and the mixture was stirred at RT for 2 h. 115 mg (0.604 mmol) of 2-chloro-5-nitropyrimidine-4,6-diamine (synthesis: Helvetica Chimica Acta (1951), 34, 835-40) were then added, and the reaction mixture was stirred at 80° C. for another 1 h. After cooling to RT, the mixture was added to water. The suspension obtained in this manner was filtered off and the solid was washed repeatedly with water and then dried under high vacuum. This gave 196 mg (77% of theory) of the title compound as a solid.

LC-MS (method 2): R$_t$=2.13 min; MS (ESIpos): m/z=399 (M+H)$^+$

Example 6A

2-[6-Fluoro-3-(2-fluorobenzyl)-1H-pyrazolo[4,3-b]pyridin-1-yl]pyrimidine-4,5,6-triamine

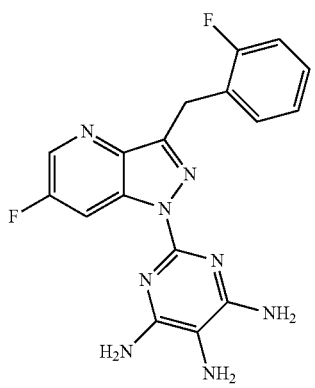 [SMILES: Nc1nc(-n2nc(Cc3ccccc3F)c3ncc(F)cc32)nc(N)c1[N+](=O)[O-]]

196 mg (0.492 mmol) of the compound from example 5A were initially charged in pyridine (22 ml), 74 mg of palladium on carbon (10% by weight) were then added and the mixture was hydrogenated at standard hydrogen pressure overnight. The reaction mixture was then filtered through kieselguhr, the filter cake was washed with ethanol and the filtrate was concentrated. The residue was triturated with ethanol at 50° C., and the solid was filtered off and dried under high vacuum. This gave 107 mg (58% of theory) of the title compound.

LC-MS (method 1): R$_t$=0.85 min; MS (ESIpos): m/z=369 (M+H)$^+$ $^1$H NMR (400 MHz, DMSO-d$_6$): δ=3.76 (s, 2H), 4.39 (s, 2H), 6.12 (s, 4H), 7.07-7.14 (m, 1H), 7.14-7.21 (m, 1H), 7.23-7.31 (m, 1H), 7.31-7.37 (m, 1H), 8.58-8.62 (m, 1H), 8.94 (dd, 1H).

WORKING EXAMPLES

Example 1

Methyl {4,6-diamino-2-[6-fluoro-3-(2-fluorobenzyl)-1H-pyrazolo[4,3-b]pyridin-1-yl]pyrimidin-5-yl}carbamate

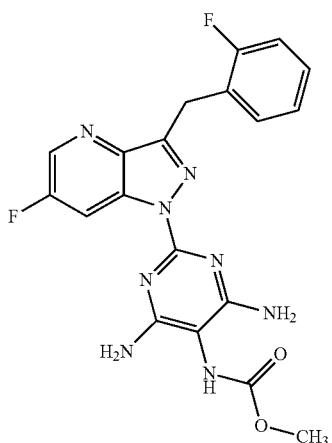

Under argon, 1.00 g (2.72 mmol) of the compound from example 6A was initially charged in pyridine (55 ml), the mixture was cooled to 0° C. and 228 µl (2.72 mmol) of methyl chloroformate (solution in 10 ml of dichloromethane) were then added dropwise. The reaction mixture was stirred further at RT overnight and then concentrated. The residue was triturated with ethanol and the solid was filtered off and dried at 50° C. under high vacuum. This gave 873 mg (75% of theory) of the title compound as a beige solid. The filtrate was re-concentrated, and purification by preparative RP-HPLC (acetonitrile:water (+0.1% formic acid)–gradient) of the residue gave a further 180 mg (16% of theory) of the title compound.

LC-MS (method 1): R$_t$=0.88 min; MS (ESIpos): m/z=427 (M+H)$^+$ $^1$H NMR (400 MHz, DMSO-d$_6$, rotamer mixture): δ [ppm]= 3.48-3.67 (m, 3H), 4.40 (s, 2H), 6.45 (br. s, 4H), 7.08-7.14

(m, 1H), 7.15-7.21 (m, 1H), 7.24-7.31 (m, 1H), 7.31-7.37 (m, 1H), 7.60 (br. s, 0.2H), 7.90 (br. s, 0.8H), 8.61-8.65 (m, 1H), 9.04 (dd, 1H).

Example 2

Ethyl {4,6-diamino-2-[6-fluoro-3-(2-fluorobenzyl)-1H-pyrazolo[4,3-b]pyridin-1-yl]pyrimidin-5-yl}carbamate

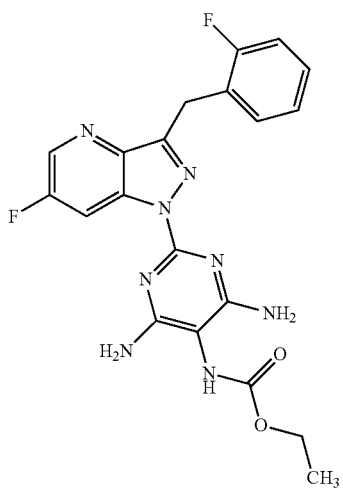 [SMILES: CCOC(=O)Nc1c(N)nc(-n2nc(Cc3ccccc3F)c3ncc(F)cc32)nc1N]

Under argon, 300 mg (0.814 mmol) of the compound from example 6A were initially charged in pyridine (10 ml), the mixture was cooled to 0° C. and 78 µl (0.814 mmol) of ethyl chloroformate were then added dropwise. The reaction mixture was stirred at 0° C. for 1 h and then concentrated. The residue was separated by means of preparative RP-HPLC (acetonitrile:water (+0.1% formic acid)–gradient) and the product fractions were concentrated. This gave 77 mg (21% of theory) of the title compound.

LC-MS (method 1): $R_t$=0.92 min; MS (ESIpos): m/z=441 (M+H)$^+$ $^1$H NMR (400 MHz, DMSO-d$_6$, rotamer mixture): δ=1.05-1.29 (m, 3H), 3.99-4.11 (m, 2H), 4.40 (s, 2H), 6.44 (br. s, 4H), 7.08-7.13 (m, 1H), 7.15-7.21 (m, 1H), 7.24-7.31 (m, 1H), 7.31-7.37 (m, 1H), 7.55 (br. s, 0.25H), 7.88 (br. s, 0.75H), 8.61-8.65 (m, 1H), 9.02-9.08 (m, 1H).

Example 3

Isopropyl {4,6-diamino-2-[6-fluoro-3-(2-fluorobenzyl)-1H-pyrazolo[4,3-b]pyridin-1-yl]pyrimidin-5-yl}carbamate

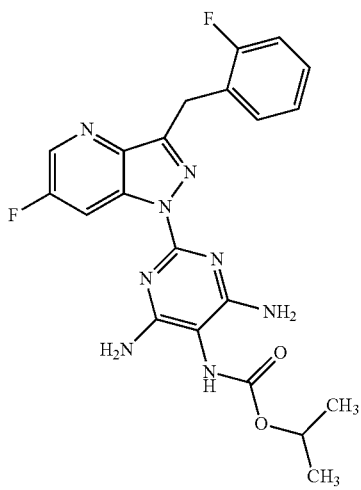 [SMILES: CC(C)OC(=O)Nc1c(N)nc(-n2nc(Cc3ccccc3F)c3ncc(F)cc32)nc1N]

The substance was prepared analogously to the synthesis of example 2 from example 6A.

Yield: 88 mg (24% of theory)

LC-MS (method 1): $R_t$=0.97 min; MS (ESIpos): m/z=455 (M+H)$^+$ $^1$H NMR (400 MHz, DMSO-d$_6$, rotamer mixture): δ [ppm]= 1.07-1.29 (m, 6H), 4.40 (s, 2H), 4.77-4.86 (m, 1H), 6.39 (br. s, 4H), 7.08-7.13 (m, 1H), 7.15-7.21 (m, 1H), 7.24-7.31 (m, 1H), 7.31-7.37 (m, 1H), 7.48 (br. s, 0.25H), 7.81 (br. s, 0.75H), 8.61-8.65 (m, 1H), 9.05 (dd, 1H).

Example 4

Cyclobutyl {4,6-diamino-2-[6-fluoro-3-(2-fluorobenzyl)-1H-pyrazolo[4,3-b]pyridin-1-yl]pyrimidin-5-yl}carbamate

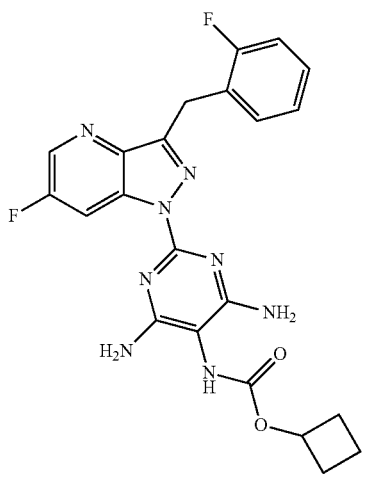 [SMILES: Nc1nc(-n2nc(Cc3ccccc3F)c3ncc(F)cc32)nc(N)c1NC(=O)OC1CCC1]

Under argon, 64 ml (0.81 mmol) of cyclobutyl alcohol were initially charged in dichloromethane (4.1 ml), 161 mg (0.54 mmol) of bis(trichloromethyl)carbonate were then added and the mixture was cooled to 0° C. 53 µl (0.65 mmol) of pyridine were then added dropwise, and the reaction mixture was stirred at 0° C. for another 30 min. 200 mg (0.54 mmol) of the compound from example 6A were then added, and the mixture was diluted with 1.4 ml of pyridine. The reaction mixture was stirred at RT overnight, saturated aqueous sodium bicarbonate solution was then added and the mixture was extracted twice with ethyl acetate. The combined organic phases were dried over sodium sulfate, filtered and concentrated. The residue was purified by means of preparative RP-HPLC (acetonitrile:water (+0.1% formic acid)–gradient) and the product fractions were concentrated.

Yield: 194 mg (77% of theory)

LC-MS (method 1): $R_t$=0.99 min; MS (ESIpos): m/z=467 (M+H)$^+$ $^1$H-NMR (400 MHz, DMSO-d$_6$, rotamer mixture): δ [ppm]=1.47-1.64 (m, 1H), 1.66-1.80 (m, 1H), 1.83-2.17 (m, 0.5H), 2.20-2.33 (m, 1.5H), 4.40 (s, 2H), 4.80-4.93 (m, 1H), 6.42 (br. s, 4H), 7.07-7.14 (m, 1H), 7.14-7.22 (m, 1H), 7.23-7.31 (m, 1H), 7.31-7.38 (m, 1H), 7.47-7.58 (m, 0.25H), 7.82-7.92 (m, 0.75H), 8.59-8.65 (m, 1H), 9.00-9.08 (m, 1H).

Example 5

Cyclopropylmethyl {4,6-diamino-2-[6-fluoro-3-(2-fluorobenzyl)-1H-pyrazolo[4,3-b]pyridin-1-yl]pyrimidin-5-yl}carbamate

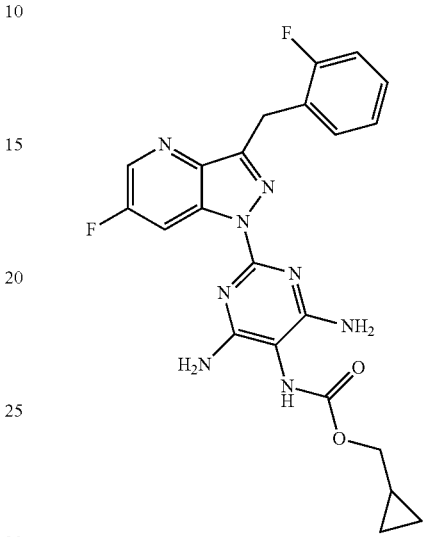

The substance was prepared analogously to the synthesis of example 4 using cyclopropylmethanol.

Yield: 191 mg (41% of theory)

LC-MS (method 1): $R_t$=0.97 min; MS (ESIpos): m/z=467 (M+H)$^+$ $^1$H-NMR (400 MHz, DMSO-d$_6$, rotamer mixture): δ [ppm]=0.18-0.36 (m, 2H), 0.37-0.59 (m, 2H), 1.08-1.19 (m, 1H), 3.82-3.88 (m, 2H), 4.40 (s, 2H), 6.42 (br. s, 4H), 7.08-7.14 (m, 1H), 7.14-7.21 (m, 1H), 7.23-7.31 (m, 1H), 7.31-7.37 (m, 1H), 7.56 (br. s, 0.25H), 7.94 (br. s, 0.75H), 8.60-8.65 (m, 1H), 9.01-9.08 (m, 1H).

Example 6

Oxetan-3-yl{4,6-diamino-2-[6-fluoro-3-(2-fluorobenzyl)-1H-pyrazolo[4,3-b]pyridin-1-yl]pyrimidin-5-yl}carbamate

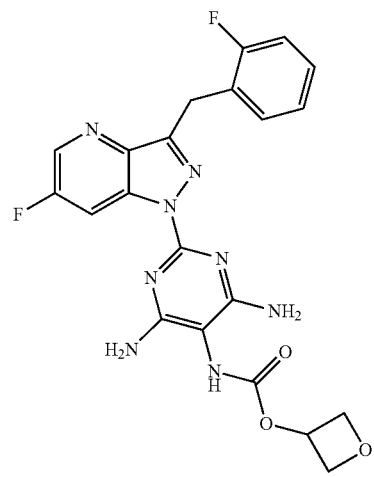 [SMILES: Nc1nc(-n2nc(Cc3ccccc3F)c3ncc(F)cc32)nc(N)c1NC(=O)OC1COC1]

Under argon, 60.4 µl (0.98 mmol) of 3-hydroxyethane were initially charged in dichloromethane (6.2 ml), 0.5 eq of bis(trichloromethyl)carbonate was then added and the mixture was cooled to 0° C. 79 µl (0.98 mmol) of pyridine were then added dropwise, and the reaction mixture was brought to RT and stirred for another 1 h. The mixture was then once more cooled to 0° C., and finally a solution of 334 mg (0.815 mmol) of the compound from example 6A in pyridine (2 ml) was added. The reaction mixture was stirred at RT overnight, saturated aqueous sodium bicarbonate solution was then added and the mixture was extracted twice with ethyl acetate. The combined organic phases were dried over sodium sulfate, filtered and concentrated. The residue was separated by means of preparative RP-HPLC (acetonitrile:water (+0.1% formic acid)-gradient) and the product fractions were concentrated. The crude product obtained in this manner was chromatographed on silica gel (dichloromethane:methanol 100:1, 30:1) and then re-purified by preparative RP-HPLC (acetonitrile:water (+0.1% formic acid)-gradient).

Yield: 19 mg (5% of theory)

LC-MS (method 1): $R_t$=0.87 min; MS (ESIpos): m/z=469 $(M+H)^+$ $^1$H NMR (400 MHz, DMSO-$d_6$, rotamer mixture): δ [ppm]= 4.40 (s, 1H), 4.43-4.48 (m, 0.5H), 4.61-4.66 (m, 1.5H), 4.67-4.73 (m, 0.5H), 4.75-4.82 (m, 1.5H), 5.26-5.38 (m, 1H), 6.45-6.63 (m, 4H), 7.07-7.14 (m, 1H), 7.15-7.22 (m, 1H), 7.24-7.31 (m, 1H), 7.31-7.37 (m, 1H), 7.78-7.82 (m, 0.25H), 8.12-8.18 (m, 0.75H), 8.61-8.66 (m, 1H), 9.01-9.09 (m, 1H).

Example 7

Methyl {4,6-diamino-2-[6-fluoro-3-(2-fluorobenzyl)-1H-pyrazolo[4,3-b]pyridin-1-yl]pyrimidin-5-yl}methylcarbamate

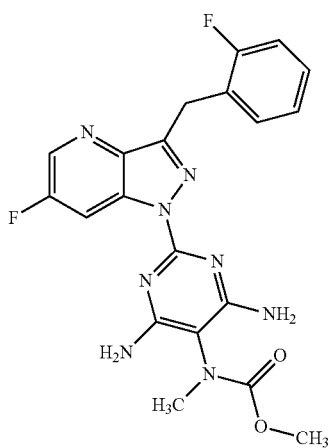 [SMILES: COC(=O)N(C)c1c(N)nc(-n2nc(Cc3ccccc3F)c3ncc(F)cc32)nc1N]

Under argon, 50 mg (0.12 mmol) of the compound from example 1 were initially charged in THF (3.3 ml), the mixture was cooled to −20° C. and 0.13 ml (0.13 mmol) of sodium bis(trimethylsilyl)amide (1.0 M in THF) was then added dropwise. The mixture was stirred at −20° C. for 30 min, and 6.6 µl (0.11 mmol) of iodomethane were then added dropwise. The reaction mixture was stirred at −20° C. for a further 10 min and at RT overnight. A further 1.0 eq of iodomethane was then added dropwise as a solution in 1.0 ml of THF, and the mixture was once more stirred at RT overnight. The reaction mixture was diluted with ethyl acetate and washed twice with saturated aqueous sodium bicarbonate solution. The organic phase was dried over magnesium sulfate, filtered and concentrated. The residue was separated by means of preparative RP-HPLC (acetonitrile:water (+0.1% formic acid)-gradient) and the product fractions were concentrated. This gave 13 mg (25% of theory) of the title compound as a solid.

LC-MS (method 1): $R_t$=0.95 min; MS (ESIpos): m/z=441 $(M+H)^+$ $^1$H NMR (400 MHz, DMSO-$d_6$, rotamer mixture): δ [ppm]= 2.99 (s, 3H), 3.53 (s, 2.1H), 3.65 (s, 0.9H), 4.40 (s, 2H), 6.63-6.70 (m, 4H), 7.08-7.13 (m, 1H), 7.15-7.21 (m, 1H), 7.23-7.36 (m, 2H), 8.61-8.65 (m, 1H), 9.04 (dd, 1H).

Example 8

Ethyl {4,6-diamino-2-[6-fluoro-3-(2-fluorobenzyl)-1H-pyrazolo[4,3-b]pyridin-1-yl]pyrimidin-5-yl}methylcarbamate

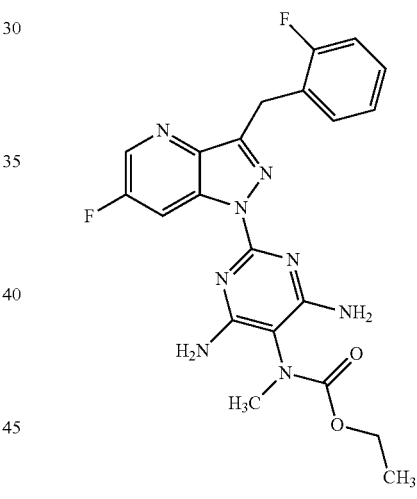

The compound was prepared analogously to the synthesis of example 7 using iodomethane and the compound from example 2. This gave 18 mg (38% of theory) of the title compound as a solid.

LC-MS (method 1): $R_t$=0.99 min; MS (ESIpos): m/z=455 $(M+H)^+$ $^1$H-NMR (400 MHz, DMSO-$d_6$, rotamer mixture): δ [ppm]=1.09 (t, 2H), 1.27 (t, 1H), 2.99 (s, 3H), 4.09 (q, 1.5H), 4.07 (q, 0.5H), 4.40 (s, 2H), 6.59-6.69 (m, 4H), 7.08-7.13 (m, 1H), 7.15-7.21 (m, 1H), 7.24-7.29 (m, 1H), 7.30-7.37 (m, 1H), 8.61-8.64 (m, 1H), 9.01-9.07 (m, 1H).

Example 9

Isopropyl {4,6-diamino-2-[6-fluoro-3-(2-fluorobenzyl)-1H-pyrazolo[4,3-b]pyridin-1-yl]pyrimidin-5-yl}methylcarbamate

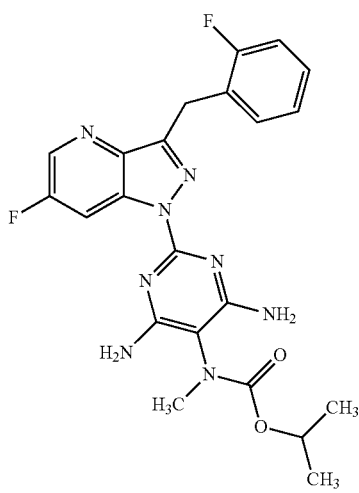 [SMILES: CC(C)OC(=O)N(C)c1c(N)nc(-n2nc(Cc3ccccc3F)c3ncc(F)cc32)nc1N]

The compound was prepared analogously to the synthesis of example 7 using iodomethane and the compound from example 3. This gave 28 mg (48% of theory) of the title compound as a solid.

LC-MS (method 1): $R_t$=0.99 min; MS (ESIpos): m/z=469 (M+H)$^+$ $^1$H-NMR (400 MHz, DMSO-d$_6$, rotamer mixture): δ [ppm]=1.10 (d, 4.5H), 1.27 (d, 1.5H), 2.98 (s, 3H), 4.39 (s, 2H), 4.75-4.84 (m, 1H), 6.55-6.66 (m, 4H), 7.08-7.14 (m, 1H), 7.15-7.21 (m, 1H), 7.24-7.37 (m, 2H), 8.61-8.65 (m, 1H), 9.02-9.08 (m, 1H).

Example 10

Methyl {4,6-diamino-2-[6-fluoro-3-(2-fluorobenzyl)-1H-pyrazolo[4,3-b]pyridin-1-yl]pyrimidin-5-yl}ethylcarbamate

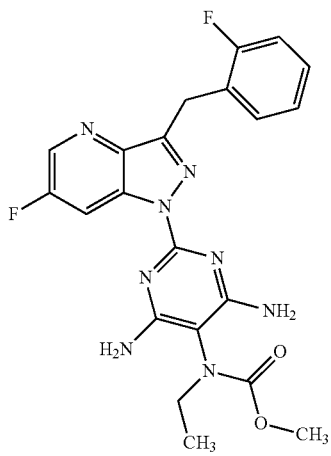 [SMILES: CCN(C(=O)OC)c1c(N)nc(-n2nc(Cc3ccccc3F)c3ncc(F)cc32)nc1N]

Under argon, 142 mg (0.33 mmol) of the compound from example 1 were initially charged in THF (9.5 ml), the mixture was cooled to 0° C. and 0.33 ml (0.33 mmol) of sodium bis(trimethylsilyl)amide (1.0 M in THF) was then added dropwise. The mixture was stirred at 0° C. for 30 min, and 35 μl (0.43 mmol) of iodoethane were then added dropwise. The reaction mixture was stirred at RT overnight. The reaction mixture was diluted with ethyl acetate and washed twice with saturated aqueous sodium bicarbonate solution. The organic phase was dried over magnesium sulfate, filtered and concentrated. The residue was chromatographed on silica gel (mobile phase dichloromethane:methanol 60:1) and the product fractions were concentrated. This gave 89 mg (59% of theory) of the title compound as a solid.

LC-MS (method 1): $R_t$=1.01 min; MS (ESIpos): m/z=455 (M+H)$^+$ $^1$H-NMR (400 MHz, DMSO-d$_6$, rotamer mixture): δ [ppm]=1.06 (t, 3H), 3.43-3.53 (m, 2H), 3.54 (s, 2H), 3.67 (s, 1H), 4.40 (s, 2H), 6.54-6.63 (m, 4H), 7.08-7.13 (m, 1H), 7.15-7.21 (m, 1H), 7.24-7.36 (m, 2H), 8.60-8.64 (m, 1H), 9.05 (dd, 1H).

Example 11

Ethyl {4,6-diamino-2-[6-fluoro-3-(2-fluorobenzyl)-1H-pyrazolo[4,3-b]pyridin-1-yl]pyrimidin-5-yl}ethylcarbamate

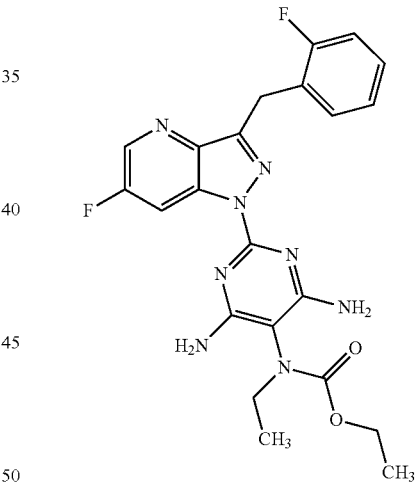

The compound was prepared analogously to the synthesis of example 10 using the compound from example 2. The compound was isolated by means of preparative RP-HPLC (acetonitrile:water (+0.1% formic acid)–gradient). This gave 38 mg (35% of theory) of the title compound as a solid.

LC-MS (method 1): $R_t$=1.05 min; MS (ESIpos): m/z=469 (M+H)$^+$ $^1$H-NMR (400 MHz, DMSO-d$_6$, rotamer mixture): δ [ppm]=1.02-1.14 (m, 5H), 1.27 (t, 1H), 3.41-3.54 (m, 2H), 3.98-4.14 (m, 2H), 4.40 (s, 2H), 6.49-6.60 (m, 4H), 7.08-7.13 (m, 1H), 7.15-7.21 (m, 1H), 7.23-7.37 (m, 2H), 8.61-8.64 (m, 1H), 9.03-9.09 (m, 1H).

Example 12

Isopropyl {4,6-diamino-2-[6-fluoro-3-(2-fluorobenzyl)-1H-pyrazolo[4,3-b]pyridin-1-yl]pyrimidin-5-yl}ethylcarbamate

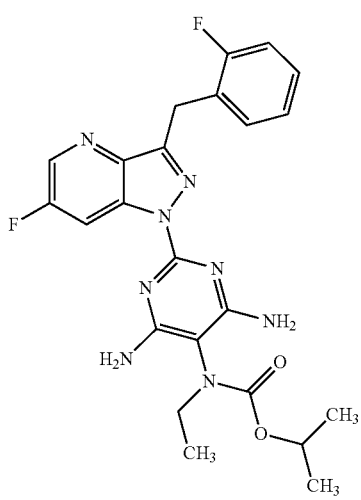 [SMILES: CCN(C(=O)OC(C)C)c1c(N)nc(-n2nc(Cc3ccccc3F)c3ncc(F)cc32)nc1N]

The compound was prepared analogously to the synthesis of example 10 using the compound from example 3. This gave 64 mg (56% of theory) of the title compound as a solid.

LC-MS (method 1): $R_t$=1.07 min; MS (ESIpos): m/z=483 (M+H)$^+$ $^1$H-NMR (400 MHz, DMSO-d$_6$, rotamer mixture): δ [ppm]=1.02-1.15 (m, 7.5H), 1.23-1.30 (m, 1.5H), 3.38-3.54 (m, 2H), 4.40 (s, 2H), 4.78-4.87 (m, 1H), 6.45-6.58 (m, 4H), 7.08-7.14 (m, 1H), 7.15-7.22 (m, 1H), 7.23-7.37 (m, 2H), 8.60-8.65 (m, 1H), 9.03-9.11 (m, 1H).

Example 13

Methyl {4,6-diamino-2-[6-fluoro-3-(2-fluorobenzyl)-1H-pyrazolo[4,3-b]pyridin-1-yl]pyrimidin-5-yl}(2,2,2-trifluoroethyl)carbamate

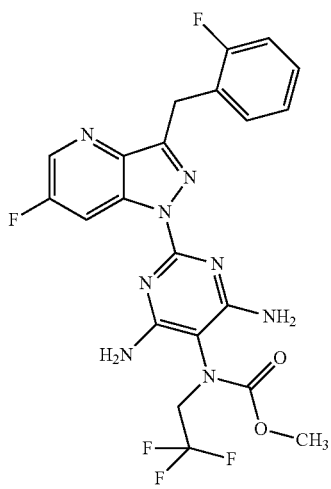 [SMILES: COC(=O)N(CC(F)(F)F)c1c(N)nc(-n2nc(Cc3ccccc3F)c3ncc(F)cc32)nc1N]

Under argon, 142 mg (0.33 mmol) of the compound from example 1 were initially charged in THF (9.5 ml), the mixture was cooled to 0° C. and 13 mg (0.33 mmol) of sodium hydride (60% suspension in mineral oil) were then added. The mixture was stirred at 0° C. for 30 min, and 96 μl (0.67 mmol) of 2,2,2,-trifluoroethyl trichloromethanesulfonate were then added dropwise. The reaction mixture was stirred at RT overnight. The mixture was then diluted with ethyl acetate and the organic phase was washed twice with saturated aqueous sodium bicarbonate solution. The organic phase was dried over magnesium sulfate, filtered and concentrated. The residue was chromatographed on silica gel (mobile phase dichloromethane:methanol 60:1) and the product fractions were concentrated. The crude product obtained in this manner was re-purified by means of preparative RP-HPLC (acetonitrile:water (+0.1% formic acid)–gradient), then suspended in acetonitrile/water and finally dried by lyophilization. This gave 68 mg (40% of theory) of the title compound as a solid.

LC-MS (method 1): $R_t$=1.05 min; MS (ESIpos): m/z=509 (M+H)$^+$ $^1$H NMR (400 MHz, DMSO-d$_6$): δ [ppm]=3.60-3.75 (m, 3H), 4.05-4.17 (m, 2H), 4.40 (s, 2H), 6.61-6.73 (m, 4H), 7.08-7.13 (m, 1H), 7.15-7.21 (m, 1H), 7.24-7.36 (m, 2H), 8.61-8.65 (m, 1H), 9.02-9.08 (m, 1H).

Example 14

Isopropyl {4,6-diamino-2-[6-fluoro-3-(2-fluorobenzyl)-1H-pyrazolo[4,3-b]pyridin-1-yl]pyrimidin-5-yl}(2,2,2-trifluoroethyl)carbamate

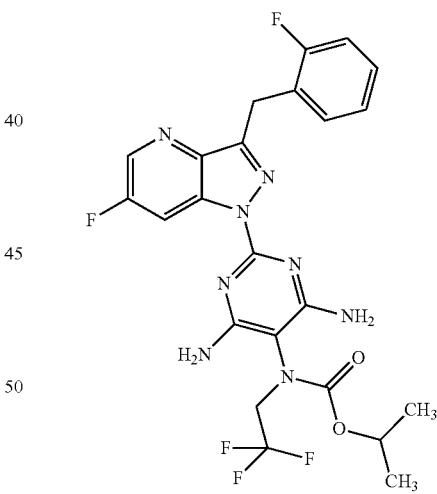

The preparation was carried out analogously to the synthesis of example 13 using the compound from example 3. The crude product was purified by means of preparative RP-HPLC (acetonitrile:water (+0.1% formic acid)–gradient) followed by preparative TLC (mobile phase dichloromethane:methanol 20:1). This gave 38 mg (30% of theory) of the title compound as a solid.

LC-MS (method 1): $R_t$=1.13 min; MS (ESIpos): m/z=537 (M+H)$^+$ $^1$H NMR (400 MHz, DMSO-d$_6$): δ [ppm]=1.09-1.33 (m, 6H), 4.03-4.16 (m, 2H), 4.40 (s, 2H), 4.81-4.91 (m, 1H), 6.52-6.67 (br s, 4H), 7.08-7.13 (m, 1H), 7.14-7.21 (m, 1H), 7.24-7.37 (m, 2H), 8.61-8.66 (m, 1H), 9.03-9.10 (m, 1H).

Example 15

Ethyl {4,6-diamino-2-[6-fluoro-3-(2-fluorobenzyl)-1H-pyrazolo[4,3-b]pyridin-1-yl]pyrimidin-5-yl}(2,2,2-trifluoroethyl)carbamate

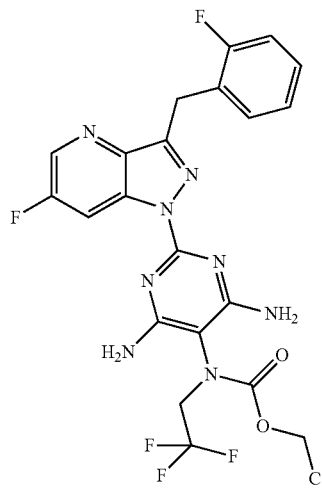

The preparation was carried out analogously to the synthesis of example 13 using the compound from example 2. The crude product was purified by means of preparative RP-HPLC (acetonitrile:water (+0.1% formic acid)–gradient). This gave 32 mg (26% of theory) of the title compound as a solid.

LC-MS (method 1): $R_t$=1.11 min; MS (ESIpos): m/z=523 $(M+H)^+$ $^1$H NMR (400 MHz, DMSO-$d_6$): δ [ppm]=1.08-1.32 (m, 3H), 4.03-4.20 (m, 4H), 4.40 (s, 2H), 6.64 (br s, 4H), 7.07-7.14 (m, 1H), 7.14-7.21 (m, 1H), 7.24-7.37 (m, 2H), 8.61-8.65 (m, 1H), 9.03-9.09 (m, 1H).

B. ASSESSMENT OF PHARMACOLOGICAL EFFICACY

The pharmacological effect of the compounds according to the invention can be shown in the following assays:

B-1. Vasorelaxant Action In Vitro

Rabbits are stunned by a blow to the neck and exsanguinated. The aorta is removed, freed from adhering tissue and divided into rings of a width of 1.5 mm. The rings are placed individually under an initial tension in 5 ml organ baths with Krebs-Henseleit solution which is at 37° C., is gassed with carbogen and has the following composition (in each case mM): sodium chloride 119; potassium chloride: 4.8; calcium chloride dihydrate: 1; magnesium sulfate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS 1802 HC, Keithley Instruments Munich), and recorded in parallel on linear recorders. To obtain a contraction, phenylephrine is added to the bath cumulatively in increasing concentration. After several control cycles, the substance to be investigated is added in each further run in increasing dosage in each case, and the height of the contraction achieved is compared with the height of the contraction reached in the last preceding run. This is used to calculate the concentration needed to reduce the magnitude of the control value by 50% ($IC_{50}$ value). The standard administration volume is 5 μl; the DMSO content in the bath solution corresponds to 0.1%.

Representative $IC_{50}$ values for the compounds according to the invention are shown in the table below (Table 1):

TABLE 1

| Example No. | $IC_{50}$ [nM] |
|---|---|
| 1 | 1380 |
| 2 | 763 |
| 7 | 194 |
| 8 | 286 |
| 13 | 178 |

B-2. Effect on a Recombinant Guanylate Cyclase Reporter Cell Line

The cellular activity of the compounds according to the invention is determined using a recombinant guanylate cyclase reporter cell line, as described in F. Wunder et al., Anal. Biochem. 339, 104-112 (2005).

Representative values (MEC=minimum effective concentration) for the compounds according to the invention are shown in the table below (Table 2):

TABLE 2

| Example No. | MEC [μM] |
|---|---|
| 1 | 0.3 |
| 2 | 0.3 |
| 7 | 0.1 |
| 8 | 0.1 |
| 13 | 0.1 |

B-3. Radiotelemetric Measurement of Blood Pressure on Conscious Spontaneously Hypertensive Rats A commercially available telemetry system from DATA SCIENCES INTERNATIONAL DSI, USA, is employed for the blood pressure measurements on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motions of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963 were a cross of male Wistar Kyoto rats with highly elevated blood pressure and female rats having a slightly elevated blood pressure and at F13 handed over to the U.S. National Institutes of Health.

After transmitter implantation, the experimental animals are housed individually in type 3 Makrolon cages. They have free access to standard feed and water.

The day/night rhythm in the experimental laboratory is changed by the room lighting at 6.00 am and at 7.00 pm.

Transmitter Implantation

The telemetry transmitters TA11 PA-C40 used are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and wound is closed layer by layer.

An antibiotic (Tardomyocel COMP, Bayer, 1 ml/kg s.c.) is administered postoperatively for prophylaxis of infection.

Substances and Solutions

Unless indicated otherwise, the substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight.

A solvent-treated group of animals is employed as control.

Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute value are corrected in the diagram with the currently measured barometric pressure (Ambient Pressure Reference Monitor; APR-1) and stored as individual data. Further technical details are given in the extensive documentation from the manufacturing company (DSI).

Unless indicated otherwise, the test substances are administered at 9.00 am on the day of the experiment. Following the administration, the parameters described above are measured over 24 hours.

Evaluation

After the end of the experiment, the acquired individual data are sorted using the analysis software (Dataquest™ A.R.T.™ Analysis). The blank value is assumed to be the time 2 hours before administration of the substance, so that the selected data set includes the period from 7.00 am on the day of the experiment to 9.00 am on the following day.

The data are smoothed over a presettable time by determination of the average (15-minute average) and transferred as a text file to a storage medium. The measured values presorted and compressed in this way are transferred into Excel templates and tabulated. For each day of the experiment, the data obtained are stored in a dedicated file carrying the number of the experiment. Results and test protocols are filed in paper form sorted by numbers.

Literature

Klaus Witte, Kai Hu, Johanna Swiatek, Claudia Müssig, Georg Ertl and Bjorn Lemme: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

B-4. Determination of Pharmacokinetic Parameters Following Intravenous and Oral Administration:

The pharmacokinetic parameters of the substance are determined in male CD-1 mice, male Wistar rats and female beagles. The administration volume is 1 ml/kg for mice, 5 ml/kg for rats and 0.5 ml/kg for dogs. Intravenous administration is via a formulation of species-specific plasma/DMSO (99/1) in the case of mice and rats and via water/PEG400/ethanol (50/40/10) in the case of dogs. The taking of blood from rats is simplified by inserting a silicone catheter into the right Vena jugularis externa prior to substance administration. The surgical intervention takes place one day prior to the experiment with isofluran anesthesia and administration of an analgetic (carprofen 5 mg/kg s.c.). Substance administration is as i.v. bolus in the case of mice and via a 15-minute infusion in the case of rats and dogs. Removal of blood is after 0, 0.033, 0.083, 0.17, 0.5, 1, 2, 3, 4, 6, 7 and 24 hours in the case of mice and after 0, 0.083, 0.25, 0.28, 0.33, 0.42, 0.75, 1, 2, 3, 4, 6, 7 and 24 hours in the case of dogs and rats. For all species, oral administration of the dissolved substance via gavage is carried out based on a water/PEG400/ethanol formulation (50/40/10). Here, the removal of blood from rats and dogs is after 0, 0.083, 0.17, 0.5, 0.75, 1, 2, 3, 4, 6, 7 and 24 hours. By contrast, oral administration is as a suspension using a 0.5% strength Tylose formulation. The blood is removed into heparinized tubes. The blood plasma is then obtained by centrifugation; if required, it can be stored at −20° C. until further processing.

An internal standard (ZK 228859) is added to the unknown samples, calibration samples and QCs, and the protein is precipitated using excess acetonitrile. After addition of a sodium acetate buffer (0.01 M, pH 6.8) and subsequent vortexing, the mixture is centrifuged at 1000 g and the supernatant is examined by LC-MS/MS (API 4000, AB Sciex). Chromatographic separation is carried out on an Agilent 1100-HPLC. The injection volume is 10 µl. The separation column used is a Phenomenex Luna 5µ C8(2) 100 A 50×2 mm, adjusted to a temperature of 40° C. A binary mobile phase gradient at 400 µl/min is used (A: 0.01M ammonium acetate buffer pH 6.8, B: 0.1% formic acid in acetonitrile): 0 min (90% A), 1 min (90% A), 3.50 min (15% A), 4.50 min (15% A), 4.60 (90% A), 7 min (90% A). The temperature of the Turbo V ion source is 500° C. The following MS instrument parameters are used: curtain gas 20 units, ion spray voltage 5 kV, gas ½ 35 units, CAD gas 40 units. The substances are quantified by peak heights or areas using extracted ion chromatograms of specific MRM experiments.

The plasma concentration/time plots determined are used to calculate the pharmacokinetic parameters such as AUC, $C_{max}$, $t_{1/2}$ (half life) and CL (clearance) employing the validated pharmacokinetic calculation program KinEx (Vers. 2.5 and 3).

Since the substance quantification is performed in plasma, it is necessary to determine the blood/plasma distribution of the substance in order to be able to adjust the pharmacokinetic parameters correspondingly. To this end, a defined amount of substance is incubated in heparinized whole blood of the species in question in a rocking roller mixer for 20 min. After centrifugation at 1000 g, the plasma concentration is measured (see above) and determined by calculating the quotient of the $c_b/c_p$ values.

Following intravenous administration of 0.3 mg/kg of example 1 in rats, the following values were recorded:

| Example | 1 |
|---|---|
| $AUC_{norm}$ [kg * h/l] | 4.62 |
| $C_{L\ blood}$ [l/h/kg] | 0.33 |
| $t_{1/2}$ [h] | 1.38 |

C. WORKING EXAMPLES OF PHARMACEUTICAL COMPOSITIONS

The compounds according to the invention can be converted to pharmaceutical formulations as follows:
Tablet:
Composition:
100 mg of the compound according to the invention, 50 mg of lactose (monohydrate), 50 mg of maize starch (native), 10 mg of polyvinylpyrrolidone (PVP 25) (BASF, Ludwigshafen, Germany) and 2 mg of magnesium stearate.
Tablet weight 212 mg, diameter 8 mm, radius of curvature 12 mm.
Production:
The mixture of the compound according to the invention, lactose and starch is granulated with a 5% solution (w/w) of the PVP in water. The granules are dried and mixed with the magnesium stearate for 5 minutes. This mixture is pressed with a conventional tableting press (for tablet dimensions see above). The guide value used for the pressing is a pressing force of 15 kN.
Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.
A single dose of 100 mg of the compound according to the invention corresponds to 10 ml of oral suspension.
Production:
The Rhodigel is suspended in ethanol; the inventive compound is added to the suspension. The water is added while stirring. The mixture is stirred for about 6 h until the swelling of the Rhodigel is complete.
Solution which can be Administered Orally:
Composition:
500 mg of the compound according to the invention, 2.5 g of polysorbate and 97 g of polyethylene glycol 400. A single dose of 100 mg of the compound according to the invention corresponds to 20 g of oral solution.
Production:
The compound according to the invention is suspended in the mixture of polyethylene glycol and polysorbate while stirring. The stirring operation is continued until dissolution of the compound according to the invention is complete.
i.v. Solution:
The compound according to the invention is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

The invention claimed is:
1. A compound of formula (I)

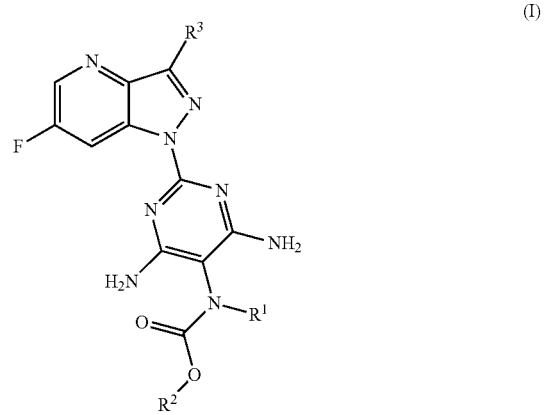

in which
$R^1$ represents hydrogen or $(C_1-C_4)$-alkyl,
where $(C_1-C_4)$-alkyl may be substituted by one or two substituents independently of one another selected from the group consisting of fluorine and trifluoromethyl,
$R^2$ represents $(C_1-C_4)$-alkyl, $(C_3-C_7)$-cycloalkyl or a 4- to 7-membered heterocycle,
where $(C_1-C_4)$-alkyl may be substituted by one or two substituents independently selected from the group consisting of fluorine, trifluoromethyl and $(C_3-C_7)$-cycloalkyl,
$R^3$ is $(C_1-C_6)$-alkyl or benzyl,
where $(C_1-C_6)$-alkyl is substituted by one trifluoromethyl substituent,
where $(C_1-C_6)$-alkyl may be substituted by 1 to 3 fluorine substituents, and
where benzyl is substituted by 1 to 3 fluorine substituents,
or a salt thereof.
2. A compound of formula (I)

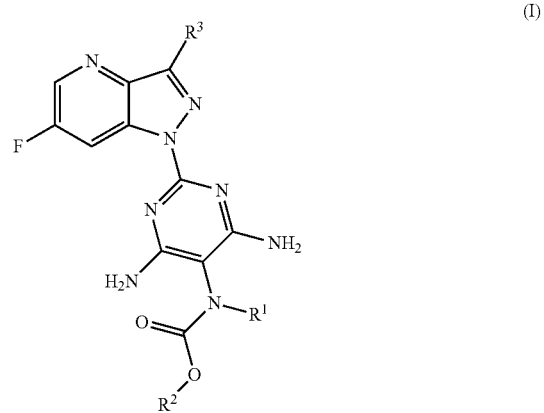

in which

R¹ represents hydrogen, methyl or ethyl,
  where methyl may be substituted by a trifluoromethyl substituent, R² represents methyl, ethyl, isopropyl, cyclopropyl, cyclobutyl or oxetanyl,
  where methyl and ethyl may be substituted by one or two substituents independently of one another selected from the group consisting of fluorine, trifluoromethyl and cyclopropyl, R³ represents 3,3,3-trifluoroprop-1-yl, 3,3,4,4,4-pentafluorobut-1-yl or benzyl,
  where benzyl is substituted by 1 or 2 fluorine substituents, or a salt thereof.

3. The compound of claim 1 in which
  R¹ represents hydrogen, methyl, ethyl or 2,2,2-trifluoroethyl,
  R² represents methyl, ethyl or cyclopropylmethyl,
  R³ represents 2-fluorobenzyl,
  or a salt thereof.

4. A pharmaceutical composition, comprising the compound of claim 1, and an inert, non-toxic, pharmaceutically acceptable excipient.

5. The pharmaceutical composition of claim 4, further comprising an active compound selected from the group consisting of an organic nitrate, an NO donor, a cGMP-PDE inhibitor, an antithrombotic agent, a hypotensive agent and a lipid metabolism modifier.

6. A method of treatment of heart failure, angina pectoris, hypertension, pulmonary hypertension, ischemias, vascular disorders, renal insufficiency, thromboembolic disorders, fibrotic disorders and arteriosclerosis comprising administering to a human or animal in need thereof an effective amount of at least one compound of claim 1.

7. A method of treatment of heart failure, angina pectoris, hypertension, pulmonary hypertension, ischemias, vascular disorders, renal insufficiency, thromboembolic disorders, fibrotic disorders and arteriosclerosis comprising administering to a human or animal in need thereof an effective amount of a pharmaceutical composition of claim 4.

8. A process for preparing a compound of formula (I) as defined in claim 1 comprising

[A] reacting a compound of formula (II)

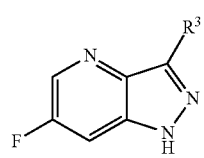

(II)

in which R³ has the meaning given in claim 1
in an inert solvent in the presence of a suitable base with a compound of formula (III)

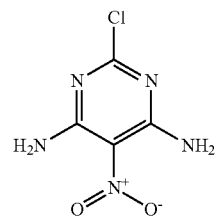

(III)

to give a compound of formula (IV)

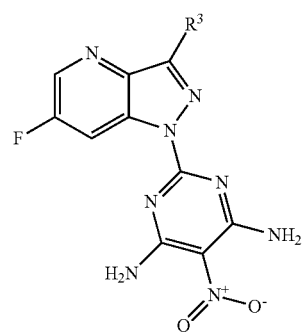

(IV)

in which R³ has the meaning given in claim 1
reducing the compound of fornnula (V) in an inert solvent with a reducing agent to give a compound of formula (V)

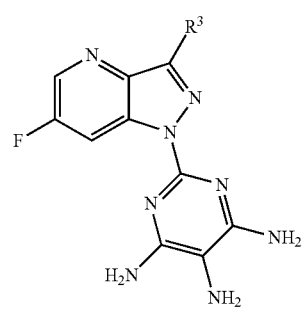

(V)

in which R³ has the meaning given in claim 1
reacting the compound of formula (V) in the presence of a suitable base in the presence or absence of a solvent with a compound of formula (VI)

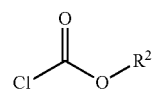

(VI)

in which R² has the meaning given in claim 1 to give a compound of formula (I-A)

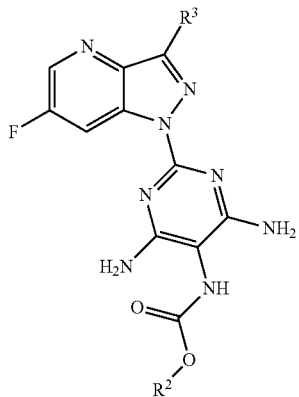
(I-A)

in which $R^2$ and $R^3$ are each as defined in claim 1,
or
[B] converting the compound of formula (II) in an inert solvent under acidic conditions with aminoacetonitrile into a compound of formula (VII)

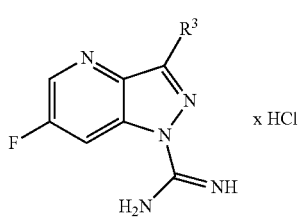
(VII)

in which $R^3$ has the meaning given in claim 1 reacting the compound of formula (VII) in an inert solvent in the presence of a suitable base with the compound of formula (VIII)

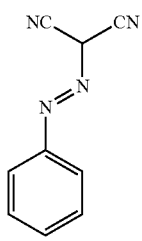
(VIII)

to give a compound of formula (IX)

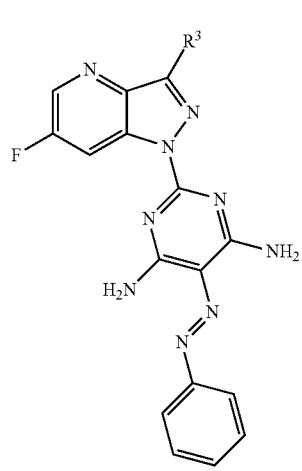
(IX)

in which $R^3$ has the meaning given in claim 1
and reducing the compound of formula (IX) in an inert solvent in the presence of a suitable reducing agent to give the compound of formula (V), and
reacting the resulting compound of formula (V) is according to process [A] to give the compound of formula (I-A),
or
[C] reacting a compound of formula (I-A) in an inert solvent with a compound of formula (X)

$$R^1\text{—}X^1 \quad \quad (X)$$

in which $R^1$ is as defined in claim 1 and
$X^1$ is a suitable leaving group,
to give a compound of formula (I-B)

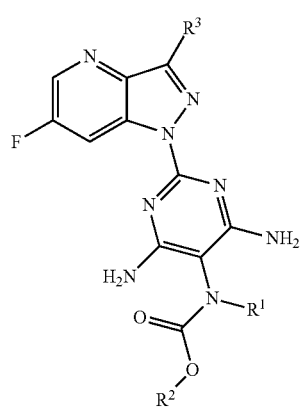
(I-B)

in which $R^1$, $R^2$ and $R^3$ are each as defined in claim 1,
and optionally converting the resulting compound of formula (I-A) or (I-B) with a (i) solvent and/or (ii) acid or base into a salt thereof.

* * * * *